United States Patent
DeBolt et al.

(10) Patent No.: US 8,383,888 B1
(45) Date of Patent: Feb. 26, 2013

(54) PLANTS AND PLANT PRODUCTS USEFUL FOR BIOFUEL MANUFACTURE AND FEEDSTOCK, AND METHODS OF PRODUCING SAME

(75) Inventors: Seth DeBolt, Nicholasville, KY (US); Darby Harris, Lexington, KY (US); Jozsef Stork, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 396 days.

(21) Appl. No.: 12/560,594

(22) Filed: Sep. 16, 2009

Related U.S. Application Data

(60) Provisional application No. 61/097,361, filed on Sep. 16, 2008.

(51) Int. Cl.
*C12S 3/04* (2006.01)
*C12P 39/00* (2006.01)
(52) U.S. Cl. ........................................ 800/284; 435/162
(58) Field of Classification Search .................. 800/284, 800/278
See application file for complete search history.

(56) References Cited

U.S. PATENT DOCUMENTS

| | | | |
|---|---|---|---|
| 6,930,225 | B2 | 8/2005 | Dhugga et al. |
| 7,241,878 | B1 | 7/2007 | Somerville et al. |
| 2005/0155108 | A1 | 7/2005 | Dhugga et al. |
| 2007/0186310 | A1 | 8/2007 | Dhugga et al. |
| 2008/0028492 | A1 | 1/2008 | Dhugga et al. |

OTHER PUBLICATIONS

Scheible et al (PNAS, Aug. 2001, vol. 98, No. 18 10079-10084).*
Sasaki et al (Biotechnology and Bioengineering, vol. XXI, pp. 1031-1047, 1979).*
Desprez et al (Plant Physiology, Feb. 2002, vol. 128, pp. 482-490).*
Tabka et al (Enzyme and Microbial Technology 36 (2006) 897-902).*
Thompson, D. L, Stalk Strength of Corn as Measured by Crushing Strength and Rind Thickness (1963) Crop Sci. 3, 323-329.
Evans, L. S., et al., Mechanical Properties and Anatomical Components of Stems of 42 Grass Species (2007) Journal of the Torrey Botanical Society 134,458-467.
Paredez et al., "Cellulose Synthase Influences Microtubule Organization, Genetic Evidence That Cellulose Synthase Activity Influences Microtubule Cortical Array Organization" Plant Physiology Preview, Published on Jun. 26, 2008.
Taylor, "Cellulose biosynthesis and deposition in higher plants" New Phytologist (2008) 178: 239-252.
Pauly et al., "Cell-wall carbohydrates and their modification as a resource for biofuels" The Plant Journal (2008) 54, 559-568.
Gomez et al. "Sustainable liquid biofuels from biomass: the writing's on the walls" New Phytologist (2008) 178: 473-485.
Desprez et al. "Organization of cellulose synthase complexes involved in primary cell wall synthesis in *Arabidopsis thaliana*" PNAS (2007) 104(39) 15572-15577.
Han et al. "Optimizing lignocellulosic feedstock for improved biofuel productivity and processing" Biofuels, Bioprod. Bioref. (2007) 1:135-146.
Rudsander "Functional studies of a membrane anchored cellulase from poplar" Royal Institute of Technology Department of Wood Biotechnology Stockholm, 2007.
NITA "Genetic mapping and molecular characterization of tbr1 mutant in *Arabidopsis thaliana*" A thesis submitted for the degree of Doctor of Philosophy (PhD) to the University of Potsdam, Jun. 2005.
Roux et al. "The Dominance of the Herbicide Resistance Cost in Several *Arabidopsis thaliana* Mutant Lines" Genetics (2004)166: 449-460.
Desprez et al. "Resistance against Herbicide Isoxaben and Cellulose Deficiency Caused by Distinct Mutations in Same Cellulose Synthase Isoform CESA6" Plant Physiology (2002) 128: 482-490.
Scheible et al. "Modifications of cellulose synthase confer resistance to isoxaben and thiazolidinone herbicides in *Arabidopsis* Ixr1 mutants" PNAS (2001) 98, 18: 10079-10084.
Harris, et al., "Genetic modification in cellulose-synthase reduces crystallinity and improves biochemical conversion to fermentable sugar" GCB Bioenergy (2009) 1: 51-71.
Heim, et al., "A second locus, lxr B1 *Arabidopsis thaliana*, that confers resistance to teh herbicide isoxaben" Plant Physiol. (1990) 92: 858-861.
Heim, et al., "Isoxaben inhibits the synthesis of acid insoluble cell wall materials in *Arabidopsis thaliana*" Plant Physiol. (1990) 93: 695-700.
Heim, et al., "Mutation of a locus of *Arabidopsis thaliana* confers resistance to the herbicide isoxaben" Plant Physiol. (1989) 90: 146-150.

* cited by examiner

*Primary Examiner* — Anne Grunberg
*Assistant Examiner* — Lee A Visone
(74) *Attorney, Agent, or Firm* — Stites & Harbison PLLC; Mandy Wilson Decker

(57) ABSTRACT

A method of processing plant cellulose includes providing plant cellulose that is from a plant expressing a CESA polypeptide variant having at least one amino acid mutation in its carboxy-terminal transmembrane region; and saccharifying the plant cellulose to produce fermentable sugars. The method can also include fermenting the fermentable sugars to produce alcohol. A method of producing a plant having beneficial saccharification properties includes introducing into a plant a polynucleotide encoding a CESA polypeptide variant having at least one amino acid mutation in its carboxy-terminal transmembrane region; and expressing in the plant the CESA polypeptide variant, wherein plant cellulose of the plant expressing the CESA polypeptide variant has beneficial saccharification properties as compared to a wild-type plant.

16 Claims, 10 Drawing Sheets

```
Betula    MSQMNFEKKF GQSAIFVTST LMEQGGVPPS SSPAALLKEA IHVISCGYED
   zea    MSQMSLEKRF GQSAAFVAST LMEYGGVPQS ATPESLLKEA IHVISCGYED
  cesa3   MSQMPLEKRF GQSAVFVAST LMENGGVPPS ATPENLLKEA IHVISCGYED
  cesa1   MSQRSVEKRF GQSPVFIAAT PMEQGGIPPT TNPATLLKEA IHVISCGYED
 populus  MSQKSFEKRF GQSPVFIAST LMENGGVPEG TNSQSHIKEA IHVISCGYEE
 solanum  MPQIKLEKKF GQSPVFVAST LLEDGGIPPG ATSASLLKEA IHVISCGYED 801                                              850
Betula    KTDNGLELGN IYGSITEDIL SGFKMHCRGN RSIYCMPKRP AFKGTAPINL
   zea    KTENGTRIGN IYGSVTEDIL TGFKMHARGN RSIYCMPERP AFKGSAPINL
  cesa3   KSDNGMEIGN IYGSVTEDIL TGFKMHARGN RSIYCMPKLP AFKGSAPINL
  cesa1   KTENGKEIGN IYGSVTEDIL TGFKMHARGN ISIYCNPPRP AFKGSAPINL
 populus  KTENGKEVGN IYGSVTEDIL TGFKMHCRGN RSVYCSPQRP AFKGSAPINL
 solanum  KTENGKEIGN IYGSVTEDIL TGFKMHCHGN RSVYCMPDRP AFKGSAPINL 851                                              900
Betula    SDRLNQVLRW ALGSIEIFFS HHCPINYGYK EGKLKWLERF SYVNTTVYPF
   zea    SDRLNQVLRW ALGSVEILFS RHCPLWYGY. QGRLKFLERF AYINTTIYPL
  cesa3   SDRLNQVLRW ALGSVEILFS RHCPINYGY. NGRLKFLERF AYVNTIYPI
  cesa1   SDRLNQVLRW ALGSIEILLS RHCPINYGY. HGRLRLLERI AYINTIVYPI
 populus  SDRLHQVLRW ALGSIEIFLS HHCPLWYGY. QGKLKLLERL AYINTIVYPF
 solanum  SDRLHQVLRW ALGSVEIFFS RHCPINYGYG CG.LKPLERF SYINSVVYPL 901                                              950
Betula    TSLPLLAYCT LPAICLLTDK FI.MPPISTF ASLYPIALPM SIFITGILEL
   zea    TSIPLLIYCI LPAICLLTGK FI.IPEISRF ASINPISLPI SIFATGILEM
  cesa3   TSIPLLMYCT LPAVCLPTNQ FI.IPQISNI ASINPLGLPL SIFATGILEM
  cesa1   TSIPLIAYCI LPAFCLITDR FI.IPEISNY ASINPILLFI SIAVTGILEL
 populus  TSIPLLAYCT IPAVCLLTGK FI.IPTLSNL ASINPLALPI SIIATSVLEL
 solanum  TSIPLIIYCT LPAVFLLTRK FNRFPEISNY ASILPNGLFI MIAVTSVIEM 951                                             1000
Betula    RWSGVTIEEN WRNEQFWVIG GVSAHLFAVF QGLLKVLAGI DTN   T
   zea    RWSGVGIDEN WRNEQFWVIG GISAHLFAVF QGLLKVLAGI DTN   T
  cesa3   RWSGVGIDEW WPNEQFWVIG GVSAHLFAVF QGILKVLAGI DTN   T
  cesa1   RWSGVSIRDN WRNEQFWVIG GTSAHLFAVF QGLLKVLAGI DTN   T
 populus  RWSGVSIQDL WRNEQFWVIG GVSAHLFAVF QGLLKVLGGV DTN   T
 solanum  QWNGVSIDDW WPNEQFWVIG GASSHLFALF QGLLKVLAGV NTS   T 1001                                            1050
Betula    TDDB.DFGBL YTPKWTTLLI PPTTILIINL VGVVAGISDA INNGYBSWGP
   zea    SDEDGDFAEL YMFKWTTLLI PPTTILIINL VGVVAGISYA INSGYQSWGP
  cesa3   SDEIXGDFAEL YLFKWTTLLI PPTTLLIVNL VGVVAGVSYA INSGYQSWGP
  cesa1   TDEDGDFAEL YIFKWTALLI PPTTVLLVNL IGIVAGVSYA VNSGYQSWGP
 populus  AD..DAEPGEL YLPKWTTLLI PPTTLIILNM VGVVAGVSDA INNGYSSWGP
 solanum  AD..DGEPSEL YLFKWTSLLI PPMTLLILNI IGVVGVSDA  INNGYDSWGP
```

FIGURE 3

Construct pKM24-CESA3-1 for expressing CESA3 in cytosol
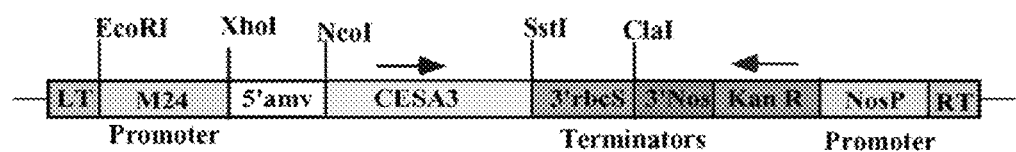
Construct pKM24-CESA3-2 for expressing CESA3 in cell wall
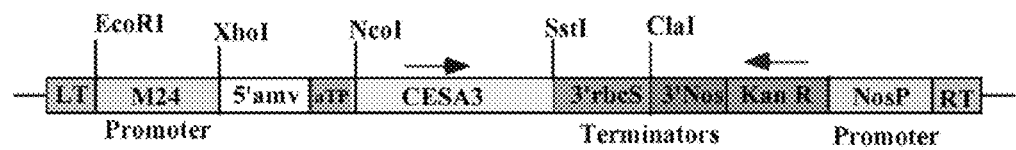
Construct pKM24-CESA3-3 for expressing fused CESA3-GFP in cell wall
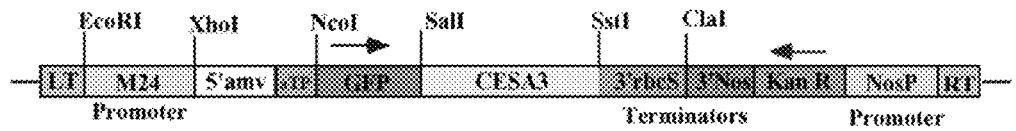
FIGURE 10

SEQUENCE LISTING

<160> NUMBER OF SEQ ID NOS: 9

<210> SEQ ID NO 1
<211> LENGTH: 3229
<212> TYPE: DNA
<213> ORGANISM: Arabidopsis thaliana

<400> SEQUENCE: 1
atggaatccg aaggagaaac cgcgggaaag ccgatgaaga acattgttcc gcagacttgc    60
cagatctgta gtgacaatgt tggcaagact gttgatggag atcgttttgt ggcttgtgat   120

```
atttgttcat tcccagtttg tcggccttgc tacgagtatg agaggaaaga tgggaatcaa    180
tcttgtcctc agtgcaaaac cagatacaag aggctcaaag gtagtcctgc tattcctggt    240
gataaagacg aggatggctt agctgatgaa ggtactgttg agttcaacta ccctcagaag    300
gagaaaattt cagagcggat gcttggttgg catcttactc gtgggaaggg agaggaaatg    360
ggggaacccc agtatgataa agaggtctct cacaatcatc ttcctcgtct cacgagcaga    420
caagatactt caggagagtt ttctgctgcc tcacctgaac gcctctctgt atcttctact    480
atcgctgggg gaaagcgcct tccctattca tcagatgtca atcaatcacc aaatagaagg    540
attgtggatc tgttggact cgggaatgta gcttggaagg agagagttga tggctggaaa    600
atgaagcaag agaagaatac tggtcctgtc agcacgcagg ctgcttctga aagaggtgga    660
gtagatattg atgccagcac agatatccta gcagatgagg ctctgctgaa tgacgaagcg    720
aggcagcctc tgtcaaggaa agtttcaatt ccttcatcac ggatcaatcc ttacagaatg    780
gttattatgc tgcggcttgt tatcctttgt ctcttcttgc attaccgtat aacaaaccca    840
gtgccaaatg cctttgctct atggctggtc tctgtgatat gtgagatctg gtttgcctta    900
tcctggattt tggatcagtt tcccaagtgg tttcctgtga accgtgaaac ctacctcgac    960
aggcttgctt taagatatga tcgtgaaggt gagccatcac agttagctgc tgttgacatt   1020
ttcgtgagta ctgttgaccc cttgaaggag ccacccttg tgacagccaa cacagtgctc   1080
tctattctgg ctgttgacta cccagttgac aaggtgtcct gttatgtttc tgatgatggt   1140
gctgctatgt tatcatttga atcacttgca gaaacatcag agtttgctcg taaatgggta   1200
ccattttgca agaaatatag catagagcct cgtgcaccag aatggtactt tgctgcgaaa   1260
atagattact tgaaggataa agttcagaca tcatttgtca agatcgtag agctatgaag   1320 agggaatatg aggaatttaa aatccgaatc aatgcacttg tttccaaagc cctaaaatgt   1380
cctgaagaag ggtgggttat gcaagatggc acaccgtggc ctggaaataa tacaagggac   1440
catccaggaa tgatccaggt cttcttaggg caaaatggtg gacttgatgc agagggcaat   1500
gagctcccgc gtttggtata tgtttctcga gaaaagcgac caggattcca gcaccacaaa   1560
aaggctggtg ctatgaatgc actggtgaga gtttcagcag ttcttaccaa tggacctttc   1620
atcttgaatc ttgattgtga tcattacata aataacagca aagccttaag agaagcaatg   1680
tgcttcctga tggacccaaa cctcgggaag caagtttgtt atgttcagtt cccacaaaga   1740
tttgatggta tcgataagaa cgatagatat gctaatcgta ataccgtgtt ctttgatatt   1800
aacttgagag gtttagatgg gattcaagga cctgtatatg tcggaactgg atgtgttttc   1860
aacagaacag cattatacgg ttatgaacct ccaataaaag taaaacacaa gaagccaagt   1920
cttttatcta agctctgtgg tggatcaaga agaagaatt ccaaagctaa gaaagagtcg   1980
gacaaaaaga aatcaggcag gcatactgac tcaactgttc ctgtattcaa cctcgatgac   2040
atagaagagg gagttgaagg tgctggtttt gatgatgaaa aggcgctctt aatgtcgcaa   2100
atgagcctgg agaagcgatt tggacagtct gctgtttttg ttgcttctac cctaatggaa   2160
aatggtggtt tcctccttc agcaactcca gaaaaccttc tcaaagaggc tatccatgtc   2220
attagttgtg gttatgagga taagtcagat tggggaatgg agattggatg gatctatggt   2280
tctgtgacag aagatattct gactgggttc aaaatgcatg cccgtggatg gcgatccatt   2340
tactgcatgc ctaagcttcc agctttcaag ggttctgctc ctatcaatct ttcagatcgt   2400
ctgaaccaag tgctgaggtg ggcttttagg tcagttgaga ttctcttcag tcggcattgt   2460
cctatatggt atggttacaa tgggaggcta aaatttcttg agaggtttgc gtatgtgaac   2520
```

-continued

```
accaccatct acccctatcac ctccattcct cttctcatgt attgtacatt gccagccgtt    2580
tgtctcttca ccaaccagtt tattattcct cagattagta acattgcaag tatatggttt    2640
ctgtctctct ttctctccat tttcgccacg ggtatactag aaatgaggtg gagtggcgta    2700
ggcatagacg aatggtggag aaacgagcag ttttgggtca ttggtggagt atccgctcat    2760
ttattcgctg tgtttcaagg tatcctcaaa gtccttgccg gtattgacac aaacttcaca    2820
gttacctcaa aagcttcaga tgaagacgga gactttgctg agctctactt gttcaaatgg    2880
acaacacttc tgattccgcc aacgacgctg ctcattgtaa acttagtggg agttgttgca    2940
ggagtctctt atgctatcaa cagtggatac caatcatggg gaccactctt tggtaagttg    3000
ttctttgcct tctgggtgat tgttcacttg tacccttttcc tcaagggttt gatgggtcga    3060
cagaaccgga ctcctaccat tgttgtggtc tggtctgttc tcttggcttc tatcttctcg    3120 tgttgtggg ttaggattga tcccttcact agccgagtca ctggcccgga cattctggaa    3180
tgtggaatca actgttgaga agcgagcaaa tatttacctg ttttgaggg                 3229
```

<210> SEQ ID NO 2
<211> LENGTH: 1065
<212> TYPE: PRT
<213> ORGANISM: Arabidopsis thaliana

<400> SEQUENCE: 2

```
Met Glu Ser Glu Gly Glu Thr Ala Gly Lys Pro Met Lys Asn Ile Val
1               5                   10                  15

Pro Gln Thr Cys Gln Ile Cys Ser Asp Asn Val Gly Lys Thr Val Asp
            20                  25                  30

Gly Asp Arg Phe Val Ala Cys Asp Ile Cys Ser Phe Pro Val Cys Arg
        35                  40                  45

Pro Cys Tyr Glu Tyr Glu Arg Lys Asp Gly Asn Gln Ser Cys Pro Gln
    50                  55                  60

Cys Lys Thr Arg Tyr Lys Arg Leu Lys Gly Ser Pro Ala Ile Pro Gly
65                  70                  75                  80

Asp Lys Asp Glu Asp Gly Leu Ala Asp Glu Gly Thr Val Glu Phe Asn
                85                  90                  95

Tyr Pro Gln Lys Glu Lys Ile Ser Glu Arg Met Leu Gly Trp His Leu
            100                 105                 110

Thr Arg Gly Lys Gly Glu Glu Met Gly Glu Pro Gln Tyr Asp Lys Glu
        115                 120                 125

Val Ser His Asn His Leu Pro Arg Leu Thr Ser Arg Gln Asp Thr Ser
    130                 135                 140

Gly Glu Phe Ser Ala Ala Ser Pro Glu Arg Leu Ser Val Ser Ser Thr
145                 150                 155                 160

Ile Ala Gly Gly Lys Arg Leu Pro Tyr Ser Ser Asp Val Asn Gln Ser
                165                 170                 175

Pro Asn Arg Arg Ile Val Asp Pro Val Gly Leu Gly Asn Val Ala Trp
            180                 185                 190

Lys Glu Arg Val Asp Gly Trp Lys Met Lys Gln Glu Lys Asn Thr Gly
        195                 200                 205

Pro Val Ser Thr Gln Ala Ala Ser Glu Arg Gly Gly Val Asp Ile Asp
    210                 215                 220

Ala Ser Thr Asp Ile Leu Ala Asp Glu Ala Leu Leu Asn Asp Glu Ala
225                 230                 235                 240

Arg Gln Pro Leu Ser Arg Lys Val Ser Ile Pro Ser Ser Arg Ile Asn
                245                 250                 255
```

```
Pro Tyr Arg Met Val Ile Met Leu Arg Leu Val Ile Leu Cys Leu Phe
            260                 265                 270

Leu His Tyr Arg Ile Thr Asn Pro Val Pro Asn Ala Phe Ala Leu Trp
            275                 280                 285

Leu Val Ser Val Ile Cys Glu Ile Trp Phe Ala Leu Ser Trp Ile Leu
            290                 295                 300

Asp Gln Phe Pro Lys Trp Phe Pro Val Asn Arg Glu Thr Tyr Leu Asp
305                 310                 315                 320

Arg Leu Ala Leu Arg Tyr Asp Arg Glu Gly Glu Pro Ser Gln Leu Ala
                325                 330                 335

Ala Val Asp Ile Phe Val Ser Thr Val Asp Pro Leu Lys Glu Pro Pro
            340                 345                 350

Leu Val Thr Ala Asn Thr Val Leu Ser Ile Leu Ala Val Asp Tyr Pro
            355                 360                 365

Val Asp Lys Val Ser Cys Tyr Val Ser Asp Asp Gly Ala Ala Met Leu
            370                 375                 380

Ser Phe Glu Ser Leu Ala Glu Thr Ser Glu Phe Ala Arg Lys Trp Val
385                 390                 395                 400

Pro Phe Cys Lys Lys Tyr Ser Ile Glu Pro Arg Ala Pro Glu Trp Tyr
                405                 410                 415

Phe Ala Ala Lys Ile Asp Tyr Leu Lys Asp Lys Val Gln Thr Ser Phe
            420                 425                 430

Val Lys Asp Arg Arg Ala Met Lys Arg Glu Tyr Glu Glu Phe Lys Ile
            435                 440                 445

Arg Ile Asn Ala Leu Val Ser Lys Ala Leu Lys Cys Pro Glu Glu Gly
            450                 455                 460

Trp Val Met Gln Asp Gly Thr Pro Trp Pro Gly Asn Asn Thr Arg Asp
465                 470                 475                 480

His Pro Gly Met Ile Gln Val Phe Leu Gly Gln Asn Gly Gly Leu Asp
                485                 490                 495

Ala Glu Gly Asn Glu Leu Pro Arg Leu Val Tyr Val Ser Arg Glu Lys
                500                 505                 510

Arg Pro Gly Phe Gln His His Lys Lys Ala Gly Ala Met Asn Ala Leu
                515                 520                 525

Val Arg Val Ser Ala Val Leu Thr Asn Gly Pro Phe Ile Leu Asn Leu
530                 535                 540

Asp Cys Asp His Tyr Ile Asn Asn Ser Lys Ala Leu Arg Glu Ala Met
545                 550                 555                 560

Cys Phe Leu Met Asp Pro Asn Leu Gly Lys Gln Val Cys Tyr Val Gln
                565                 570                 575

Phe Pro Gln Arg Phe Asp Gly Ile Asp Lys Asn Asp Arg Tyr Ala Asn
                580                 585                 590

Arg Asn Thr Val Phe Phe Asp Ile Asn Leu Arg Gly Leu Asp Gly Ile
            595                 600                 605

Gln Gly Pro Val Tyr Val Gly Thr Gly Cys Val Phe Asn Arg Thr Ala
            610                 615                 620

Leu Tyr Gly Tyr Glu Pro Pro Ile Lys Val Lys His Lys Lys Pro Ser
625                 630                 635                 640

Leu Leu Ser Lys Leu Cys Gly Gly Ser Arg Lys Lys Asn Ser Lys Ala
                645                 650                 655

Lys Lys Glu Ser Asp Lys Lys Ser Gly Arg His Thr Asp Ser Thr
                660                 665                 670

Val Pro Val Phe Asn Leu Asp Asp Ile Glu Glu Gly Val Glu Gly Ala
            675                 680                 685
```

-continued

Gly Phe Asp Asp Glu Lys Ala Leu Leu Met Ser Gln Met Ser Leu Glu
    690                 695                 700

Lys Arg Phe Gly Gln Ser Ala Val Phe Val Ala Ser Thr Leu Met Glu
705                 710                 715                 720

Asn Gly Gly Val Pro Pro Ser Ala Thr Pro Glu Asn Leu Leu Lys Glu
                725                 730                 735

Ala Ile His Val Ile Ser Cys Gly Tyr Glu Asp Lys Ser Asp Trp Gly
            740                 745                 750

Met Glu Ile Gly Trp Ile Tyr Gly Ser Val Thr Glu Asp Ile Leu Thr
        755                 760                 765

Gly Phe Lys Met His Ala Arg Gly Trp Arg Ser Ile Tyr Cys Met Pro
770                 775                 780

Lys Leu Pro Ala Phe Lys Gly Ser Ala Pro Ile Asn Leu Ser Asp Arg
785                 790                 795                 800

Leu Asn Gln Val Leu Arg Trp Ala Leu Gly Ser Val Glu Ile Leu Phe
                805                 810                 815

Ser Arg His Cys Pro Ile Trp Tyr Gly Tyr Asn Gly Arg Leu Lys Phe
            820                 825                 830

Leu Glu Arg Phe Ala Tyr Val Asn Thr Thr Ile Tyr Pro Ile Thr Ser
        835                 840                 845

Ile Pro Leu Leu Met Tyr Cys Thr Leu Pro Ala Val Cys Leu Phe Thr
850                 855                 860

Asn Gln Phe Ile Ile Pro Gln Ile Ser Asn Ile Ala Ser Ile Trp Phe
865                 870                 875                 880

Leu Ser Leu Phe Leu Ser Ile Phe Ala Thr Gly Ile Leu Glu Met Arg
                885                 890                 895

Trp Ser Gly Val Gly Ile Asp Glu Trp Trp Arg Asn Glu Gln Phe Trp
            900                 905                 910

Val Ile Gly Gly Val Ser Ala His Leu Phe Ala Val Phe Gln Gly Ile
        915                 920                 925

Leu Lys Val Leu Ala Gly Ile Asp Thr Asn Phe Thr Val Thr Ser Lys
930                 935                 940

Ala Ser Asp Glu Asp Gly Asp Phe Ala Glu Leu Tyr Leu Phe Lys Trp
945                 950                 955                 960

Thr Thr Leu Leu Ile Pro Pro Thr Thr Leu Leu Ile Val Asn Leu Val
                965                 970                 975

Gly Val Val Ala Gly Val Ser Tyr Ala Ile Asn Ser Gly Tyr Gln Ser
            980                 985                 990

Trp Gly Pro Leu Phe Gly Lys Leu Phe Phe Ala Phe Trp Val Ile Val
        995                 1000                1005

His Leu Tyr Pro Phe Leu Lys Gly Leu Met Gly Arg Gln Asn Arg
    1010                1015                1020

Thr Pro Thr Ile Val Val Trp Ser Val Leu Leu Ala Ser Ile
    1025                1030                1035

Phe Ser Leu Leu Trp Val Arg Ile Asp Pro Phe Thr Ser Arg Val
    1040                1045                1050

Thr Gly Pro Asp Ile Leu Glu Cys Gly Ile Asn Cys
    1055                1060                1065

<210> SEQ ID NO 3
<211> LENGTH: 1065
<212> TYPE: PRT
<213> ORGANISM: Arabidopsis thaliana

<400> SEQUENCE: 3

-continued

```
Met Glu Ser Glu Gly Glu Thr Ala Gly Lys Pro Met Lys Asn Ile Val
1               5                   10                  15

Pro Gln Thr Cys Gln Ile Cys Ser Asp Asn Val Gly Lys Thr Val Asp
            20                  25                  30

Gly Asp Arg Phe Val Ala Cys Asp Ile Cys Ser Phe Pro Val Cys Arg
            35                  40                  45

Pro Cys Tyr Glu Tyr Glu Arg Lys Asp Gly Asn Gln Ser Cys Pro Gln
    50                  55                  60

Cys Lys Thr Arg Tyr Lys Arg Leu Lys Gly Ser Pro Ala Ile Pro Gly
65                  70                  75                  80

Asp Lys Asp Glu Asp Gly Leu Ala Asp Glu Gly Thr Val Glu Phe Asn
                85                  90                  95

Tyr Pro Gln Lys Glu Lys Ile Ser Glu Arg Met Leu Gly Trp His Leu
                100                 105                 110

Thr Arg Gly Lys Gly Glu Glu Met Gly Glu Pro Gln Tyr Asp Lys Glu
            115                 120                 125

Val Ser His Asn His Leu Pro Arg Leu Thr Ser Arg Gln Asp Thr Ser
            130                 135                 140

Gly Glu Phe Ser Ala Ala Ser Pro Glu Arg Leu Ser Val Ser Ser Thr
145                 150                 155                 160

Ile Ala Gly Gly Lys Arg Leu Pro Tyr Ser Ser Asp Val Asn Gln Ser
                165                 170                 175

Pro Asn Arg Arg Ile Val Asp Pro Val Gly Leu Gly Asn Val Ala Trp
            180                 185                 190

Lys Glu Arg Val Asp Gly Trp Lys Met Lys Gln Glu Lys Asn Thr Gly
            195                 200                 205

Pro Val Ser Thr Gln Ala Ala Ser Glu Arg Gly Gly Val Asp Ile Asp
            210                 215                 220

Ala Ser Thr Asp Ile Leu Ala Asp Glu Ala Leu Leu Asn Asp Glu Ala
225                 230                 235                 240

Arg Gln Pro Leu Ser Arg Lys Val Ser Ile Pro Ser Ser Arg Ile Asn
                245                 250                 255

Pro Tyr Arg Met Val Ile Met Leu Arg Leu Val Ile Leu Cys Leu Phe
            260                 265                 270

Leu His Tyr Arg Ile Thr Asn Pro Val Pro Asn Ala Phe Ala Leu Trp
            275                 280                 285

Leu Val Ser Val Ile Cys Glu Ile Trp Phe Ala Leu Ser Trp Ile Leu
            290                 295                 300

Asp Gln Phe Pro Lys Trp Phe Pro Val Asn Arg Glu Thr Tyr Leu Asp
305                 310                 315                 320

Arg Leu Ala Leu Arg Tyr Asp Arg Glu Gly Glu Pro Ser Gln Leu Ala
                325                 330                 335

Ala Val Asp Ile Phe Val Ser Thr Val Asp Pro Leu Lys Glu Pro Pro
            340                 345                 350

Leu Val Thr Ala Asn Thr Val Leu Ser Ile Leu Ala Val Asp Tyr Pro
            355                 360                 365

Val Asp Lys Val Ser Cys Tyr Val Ser Asp Asp Gly Ala Ala Met Leu
            370                 375                 380

Ser Phe Glu Ser Leu Ala Glu Thr Ser Glu Phe Ala Arg Lys Trp Val
385                 390                 395                 400

Pro Phe Cys Lys Lys Tyr Ser Ile Glu Pro Arg Ala Pro Glu Trp Tyr
                405                 410                 415

Phe Ala Ala Lys Ile Asp Tyr Leu Lys Asp Lys Val Gln Thr Ser Phe
```

```
                420             425             430
Val Lys Asp Arg Arg Ala Met Lys Arg Glu Tyr Glu Glu Phe Lys Ile
            435                 440                 445
Arg Ile Asn Ala Leu Val Ser Lys Ala Leu Lys Cys Pro Glu Glu Gly
            450                 455                 460
Trp Val Met Gln Asp Gly Thr Pro Trp Pro Gly Asn Asn Thr Arg Asp
465                 470                 475                 480
His Pro Gly Met Ile Gln Val Phe Leu Gly Gln Asn Gly Gly Leu Asp
                485                 490                 495
Ala Glu Gly Asn Glu Leu Pro Arg Leu Val Tyr Val Ser Arg Glu Lys
            500                 505                 510
Arg Pro Gly Phe Gln His His Lys Lys Ala Gly Ala Met Asn Ala Leu
            515                 520                 525
Val Arg Val Ser Ala Val Leu Thr Asn Gly Pro Phe Ile Leu Asn Leu
            530                 535                 540
Asp Cys Asp His Tyr Ile Asn Asn Ser Lys Ala Leu Arg Glu Ala Met
545                 550                 555                 560
Cys Phe Leu Met Asp Pro Asn Leu Gly Lys Gln Val Cys Tyr Val Gln
                565                 570                 575
Phe Pro Gln Arg Phe Asp Gly Ile Asp Lys Asn Asp Arg Tyr Ala Asn
                580                 585                 590
Arg Asn Thr Val Phe Phe Asp Ile Asn Leu Arg Gly Leu Asp Gly Ile
            595                 600                 605
Gln Gly Pro Val Tyr Val Gly Thr Gly Cys Val Phe Asn Arg Thr Ala
            610                 615                 620
Leu Tyr Gly Tyr Glu Pro Pro Ile Lys Val Lys His Lys Lys Pro Ser
625                 630                 635                 640
Leu Leu Ser Lys Leu Cys Gly Gly Ser Arg Lys Lys Asn Ser Lys Ala
                645                 650                 655
Lys Lys Glu Ser Asp Lys Lys Ser Gly Arg His Thr Asp Ser Thr
                660                 665                 670
Val Pro Val Phe Asn Leu Asp Asp Ile Glu Glu Gly Val Glu Gly Ala
            675                 680                 685
Gly Phe Asp Asp Glu Lys Ala Leu Leu Met Ser Gln Met Ser Leu Glu
            690                 695                 700
Lys Arg Phe Gly Gln Ser Ala Val Phe Val Ala Ser Thr Leu Met Glu
705                 710                 715                 720
Asn Gly Gly Val Pro Pro Ser Ala Thr Pro Glu Asn Leu Leu Lys Glu
                725                 730                 735
Ala Ile His Val Ile Ser Cys Gly Tyr Glu Asp Lys Ser Asp Trp Gly
                740                 745                 750
Met Glu Ile Gly Trp Ile Tyr Gly Ser Val Thr Glu Asp Ile Leu Thr
            755                 760                 765
Gly Phe Lys Met His Ala Arg Gly Trp Arg Ser Ile Tyr Cys Met Pro
            770                 775                 780
Lys Leu Pro Ala Phe Lys Gly Ser Ala Pro Ile Asn Leu Ser Asp Arg
785                 790                 795                 800
Leu Asn Gln Val Leu Arg Trp Ala Leu Gly Ser Val Glu Ile Leu Phe
                805                 810                 815
Ser Arg His Cys Pro Ile Trp Tyr Gly Tyr Asn Gly Arg Leu Lys Phe
                820                 825                 830
Leu Glu Arg Phe Ala Tyr Val Asn Thr Thr Ile Tyr Pro Ile Thr Ser
            835                 840                 845
```

```
Ile Pro Leu Leu Met Tyr Cys Thr Leu Pro Ala Val Cys Leu Phe Thr
        850                 855                 860

Asn Gln Phe Ile Ile Pro Gln Ile Ser Asn Ile Ala Ser Ile Trp Phe
865                 870                 875                 880

Leu Ser Leu Phe Leu Ser Ile Phe Ala Thr Gly Ile Leu Glu Met Arg
                885                 890                 895

Trp Ser Gly Val Gly Ile Asp Glu Trp Trp Arg Asn Glu Gln Phe Trp
                900                 905                 910

Val Ile Gly Gly Val Ser Ala His Leu Phe Ala Val Phe Gln Gly Ile
            915                 920                 925

Leu Lys Val Leu Ala Gly Ile Asp Thr Asn Phe Thr Val Ile Ser Lys
    930                 935                 940

Ala Ser Asp Glu Asp Gly Asp Phe Ala Glu Leu Tyr Leu Phe Lys Trp
945                 950                 955                 960

Thr Thr Leu Leu Ile Pro Pro Thr Thr Leu Leu Ile Val Asn Leu Val
                965                 970                 975

Gly Val Val Ala Gly Val Ser Tyr Ala Ile Asn Ser Gly Tyr Gln Ser
            980                 985                 990

Trp Gly Pro Leu Phe Gly Lys Leu Phe Phe Ala Phe Trp Val Ile Val
        995                 1000                1005

His Leu Tyr Pro Phe Leu Lys  Gly Leu Met Gly Arg  Gln Asn Arg
    1010                1015                1020

Thr Pro Thr Ile Val Val Val  Trp Ser Val Leu Leu  Ala Ser Ile
    1025                1030                1035

Phe Ser Leu Leu Trp Val Arg  Ile Asp Pro Phe Thr  Ser Arg Val
    1040                1045                1050

Thr Gly Pro Asp Ile Leu Glu  Cys Gly Ile Asn Cys
    1055                1060                1065

<210> SEQ ID NO 4
<211> LENGTH: 298
<212> TYPE: PRT
<213> ORGANISM: Betula pendula

<400> SEQUENCE: 4

Met Ser Gln Met Asn Phe Glu Lys Lys Phe Gly Gln Ser Ala Ile Phe
1               5                   10                  15

Val Thr Ser Thr Leu Met Glu Gln Gly Val Pro Ser Ser Ser
            20                  25                  30

Pro Ala Ala Leu Leu Lys Glu Ala Ile His Val Ile Ser Cys Gly Tyr
            35                  40                  45

Glu Asp Lys Thr Asp Trp Gly Leu Glu Leu Gly Trp Ile Tyr Gly Ser
50                  55                  60

Ile Thr Glu Asp Ile Leu Ser Gly Phe Lys Met His Cys Arg Gly Trp
65                  70                  75                  80

Arg Ser Ile Tyr Cys Met Pro Lys Arg Pro Ala Phe Lys Gly Thr Ala
                85                  90                  95

Pro Ile Asn Leu Ser Asp Arg Leu Asn Gln Val Leu Arg Trp Ala Leu
            100                 105                 110

Gly Ser Ile Glu Ile Phe Phe Ser His His Cys Pro Ile Trp Tyr Gly
            115                 120                 125

Tyr Lys Glu Gly Lys Leu Lys Trp Leu Glu Arg Phe Ser Tyr Val Asn
    130                 135                 140

Thr Thr Val Tyr Pro Phe Thr Ser Leu Pro Leu Leu Ala Tyr Cys Thr
145                 150                 155                 160
```

```
Leu Pro Ala Ile Cys Leu Leu Thr Asp Lys Phe Ile Met Pro Pro Ile
            165                 170                 175

Ser Thr Phe Ala Ser Leu Tyr Phe Ile Ala Leu Phe Met Ser Ile Phe
            180                 185                 190

Ile Thr Gly Ile Leu Glu Leu Arg Trp Ser Gly Val Thr Ile Glu Glu
            195                 200                 205

Trp Trp Arg Asn Glu Gln Phe Trp Val Ile Gly Gly Val Ser Ala His
            210                 215                 220

Leu Phe Ala Val Phe Gln Gly Leu Leu Lys Val Leu Ala Gly Ile Asp
225                 230                 235                 240

Thr Asn Phe Thr Val Thr Ser Lys Ala Thr Asp Glu Asp Phe Gly
            245                 250                 255

Glu Leu Tyr Thr Phe Lys Trp Thr Thr Leu Leu Ile Pro Pro Thr Thr
            260                 265                 270

Ile Leu Ile Ile Asn Leu Val Gly Val Val Ala Gly Ile Ser Asp Ala
            275                 280                 285

Ile Asn Asn Gly Tyr Glu Ser Trp Gly Pro
            290                 295

<210> SEQ ID NO 5
<211> LENGTH: 298
<212> TYPE: PRT
<213> ORGANISM: Zea mays

<400> SEQUENCE: 5

Met Ser Gln Met Ser Leu Glu Lys Arg Phe Gly Gln Ser Ala Ala Phe
1               5                   10                  15

Val Ala Ser Thr Leu Met Glu Tyr Gly Gly Val Pro Gln Ser Ala Thr
            20                  25                  30

Pro Glu Ser Leu Leu Lys Glu Ala Ile His Val Ile Ser Cys Gly Tyr
            35                  40                  45

Glu Asp Lys Thr Glu Trp Gly Thr Glu Ile Gly Trp Ile Tyr Gly Ser
        50                  55                  60

Val Thr Glu Asp Ile Leu Thr Gly Phe Lys Met His Ala Arg Gly Trp
65                  70                  75                  80

Arg Ser Ile Tyr Cys Met Pro Lys Arg Pro Ala Phe Lys Gly Ser Ala
                85                  90                  95

Pro Ile Asn Leu Ser Asp Arg Leu Asn Gln Val Leu Arg Trp Ala Leu
            100                 105                 110

Gly Ser Val Glu Ile Leu Phe Ser Arg His Cys Pro Leu Trp Tyr Gly
            115                 120                 125

Tyr Gly Gly Arg Leu Lys Phe Leu Glu Arg Phe Ala Tyr Ile Asn Thr
            130                 135                 140

Thr Ile Tyr Pro Leu Thr Ser Ile Pro Leu Leu Ile Tyr Cys Ile Leu
145                 150                 155                 160

Pro Ala Ile Cys Leu Leu Thr Gly Lys Phe Ile Ile Pro Glu Ile Ser
            165                 170                 175

Asn Phe Ala Ser Ile Trp Phe Ile Ser Leu Phe Ile Ser Ile Phe Ala
            180                 185                 190

Thr Gly Ile Leu Glu Met Arg Trp Ser Gly Val Gly Ile Asp Glu Trp
            195                 200                 205

Trp Arg Asn Glu Gln Phe Trp Val Ile Gly Gly Ile Ser Ala His Leu
            210                 215                 220

Phe Ala Val Phe Gln Gly Leu Leu Lys Val Leu Ala Gly Ile Asp Thr
225                 230                 235                 240
```

```
Asn Phe Thr Val Thr Ser Lys Ala Ser Asp Glu Asp Gly Asp Phe Ala
            245                 250                 255

Glu Leu Tyr Met Phe Lys Trp Thr Thr Leu Leu Ile Pro Pro Thr Thr
            260                 265                 270

Ile Leu Ile Ile Asn Leu Val Gly Val Val Ala Gly Ile Ser Tyr Ala
            275                 280                 285

Ile Asn Ser Gly Tyr Gln Ser Trp Gly Pro
            290                 295

<210> SEQ ID NO 6
<211> LENGTH: 298
<212> TYPE: PRT
<213> ORGANISM: Arabidopsis thaliana

<400> SEQUENCE: 6

Met Ser Gln Met Ser Leu Glu Lys Arg Phe Gly Gln Ser Ala Val Phe
1               5                   10                  15

Val Ala Ser Thr Leu Met Glu Asn Gly Gly Val Pro Pro Ser Ala Thr
            20                  25                  30

Pro Glu Asn Leu Leu Lys Glu Ala Ile His Val Ile Ser Cys Gly Tyr
            35                  40                  45

Glu Asp Lys Ser Asp Trp Gly Met Glu Ile Gly Trp Ile Tyr Gly Ser
50                  55                  60

Val Thr Glu Asp Ile Leu Thr Gly Phe Lys Met His Ala Arg Gly Trp
65                  70                  75                  80

Arg Ser Ile Tyr Cys Met Pro Lys Leu Pro Ala Phe Lys Gly Ser Ala
                85                  90                  95

Pro Ile Asn Leu Ser Asp Arg Leu Asn Gln Val Leu Arg Trp Ala Leu
            100                 105                 110

Gly Ser Val Glu Ile Leu Phe Ser Arg His Cys Pro Ile Trp Tyr Gly
            115                 120                 125

Tyr Asn Gly Arg Leu Lys Phe Leu Glu Arg Phe Ala Tyr Val Asn Thr
            130                 135                 140

Thr Ile Tyr Pro Ile Thr Ser Ile Pro Leu Leu Met Tyr Cys Thr Leu
145                 150                 155                 160

Pro Ala Val Cys Leu Phe Thr Asn Gln Phe Ile Ile Pro Gln Ile Ser
                165                 170                 175

Asn Ile Ala Ser Ile Trp Phe Leu Ser Leu Phe Leu Ser Ile Phe Ala
            180                 185                 190

Thr Gly Ile Leu Glu Met Arg Trp Ser Gly Val Gly Ile Asp Glu Trp
            195                 200                 205

Trp Arg Asn Glu Gln Phe Trp Val Ile Gly Gly Val Ser Ala His Leu
            210                 215                 220

Phe Ala Val Phe Gln Gly Ile Leu Lys Val Leu Ala Gly Ile Asp Thr
225                 230                 235                 240

Asn Phe Thr Val Thr Ser Lys Ala Ser Asp Glu Asp Gly Asp Phe Ala
            245                 250                 255

Glu Leu Tyr Leu Phe Lys Trp Thr Thr Leu Leu Ile Pro Pro Thr Thr
            260                 265                 270

Leu Leu Ile Val Asn Leu Val Gly Val Val Ala Gly Val Ser Tyr Ala
            275                 280                 285

Ile Asn Ser Gly Tyr Gln Ser Trp Gly Pro
            290                 295

<210> SEQ ID NO 7
<211> LENGTH: 298
```

```
<212> TYPE: PRT
<213> ORGANISM: Arabidopsis thaliana

<400> SEQUENCE: 7

Met Ser Gln Arg Ser Val Glu Lys Arg Phe Gly Gln Ser Pro Val Phe
1               5                   10                  15

Ile Ala Ala Thr Phe Met Glu Gln Gly Gly Ile Pro Pro Thr Thr Asn
            20                  25                  30

Pro Ala Thr Leu Leu Lys Glu Ala Ile His Val Ile Ser Cys Gly Tyr
        35                  40                  45

Glu Asp Lys Thr Glu Trp Gly Lys Glu Ile Gly Trp Ile Tyr Gly Ser
    50                  55                  60

Val Thr Glu Asp Ile Leu Thr Gly Phe Lys Met His Ala Arg Gly Trp
65                  70                  75                  80

Ile Ser Ile Tyr Cys Asn Pro Pro Arg Pro Ala Phe Lys Gly Ser Ala
                85                  90                  95

Pro Ile Asn Leu Ser Asp Arg Leu Asn Gln Val Leu Arg Trp Ala Leu
            100                 105                 110

Gly Ser Ile Glu Ile Leu Leu Ser Arg His Cys Pro Ile Trp Tyr Gly
        115                 120                 125

Tyr His Gly Arg Leu Arg Leu Leu Glu Arg Ile Ala Tyr Ile Asn Thr
    130                 135                 140

Ile Val Tyr Pro Ile Thr Ser Ile Pro Leu Ile Ala Tyr Cys Ile Leu
145                 150                 155                 160

Pro Ala Phe Cys Leu Ile Thr Asp Arg Phe Ile Ile Pro Glu Ile Ser
                165                 170                 175

Asn Tyr Ala Ser Ile Trp Phe Ile Leu Leu Phe Ile Ser Ile Ala Val
            180                 185                 190

Thr Gly Ile Leu Glu Leu Arg Trp Ser Gly Val Ser Ile Glu Asp Trp
        195                 200                 205

Trp Arg Asn Glu Gln Phe Trp Val Ile Gly Gly Thr Ser Ala His Leu
    210                 215                 220

Phe Ala Val Phe Gln Gly Leu Leu Lys Val Leu Ala Gly Ile Asp Thr
225                 230                 235                 240

Asn Phe Thr Val Thr Ser Lys Ala Thr Asp Glu Asp Gly Asp Phe Ala
                245                 250                 255

Glu Leu Tyr Ile Phe Lys Trp Thr Ala Leu Leu Ile Pro Pro Thr Thr
            260                 265                 270

Val Leu Leu Val Asn Leu Ile Gly Ile Val Ala Gly Val Ser Tyr Ala
        275                 280                 285

Val Asn Ser Gly Tyr Gln Ser Trp Gly Pro
    290                 295

<210> SEQ ID NO 8
<211> LENGTH: 297
<212> TYPE: PRT
<213> ORGANISM: Populus trichocarpa

<400> SEQUENCE: 8

Met Ser Gln Lys Ser Phe Glu Lys Arg Phe Gly Gln Ser Pro Val Phe
1               5                   10                  15

Ile Ala Ser Thr Leu Met Glu Asn Gly Gly Val Pro Glu Gly Thr Asn
            20                  25                  30

Ser Gln Ser His Ile Lys Glu Ala Ile His Val Ile Ser Cys Gly Tyr
        35                  40                  45

Glu Glu Lys Thr Glu Trp Gly Lys Glu Val Gly Trp Ile Tyr Gly Ser
```

```
                50                  55                  60
Val Thr Glu Asp Ile Leu Thr Gly Phe Lys Met His Cys Arg Gly Trp
 65                  70                  75                  80

Arg Ser Val Tyr Cys Ser Pro Gln Arg Pro Ala Phe Lys Gly Ser Ala
                 85                  90                  95

Pro Ile Asn Leu Ser Asp Arg Leu His Gln Val Leu Arg Trp Ala Leu
            100                 105                 110

Gly Ser Ile Glu Ile Phe Leu Ser His His Cys Pro Leu Trp Tyr Gly
        115                 120                 125

Tyr Gly Gly Lys Leu Lys Leu Leu Glu Arg Leu Ala Tyr Ile Asn Thr
    130                 135                 140

Ile Val Tyr Pro Phe Thr Ser Ile Pro Leu Leu Ala Tyr Cys Thr Ile
145                 150                 155                 160

Pro Ala Val Cys Leu Leu Thr Gly Lys Phe Ile Ile Pro Thr Leu Asn
                165                 170                 175

Asn Leu Ala Ser Ile Trp Phe Leu Ala Leu Phe Ile Ser Ile Ile Ala
            180                 185                 190

Thr Ser Val Leu Glu Leu Arg Trp Ser Gly Val Ser Ile Gln Asp Leu
        195                 200                 205

Trp Arg Asn Glu Gln Phe Trp Val Ile Gly Val Ser Ala His Leu
    210                 215                 220

Phe Ala Val Phe Gln Gly Leu Leu Lys Val Leu Gly Val Asp Thr
225                 230                 235                 240

Asn Phe Thr Val Thr Ser Lys Ser Ala Asp Asp Ala Glu Phe Gly Glu
                245                 250                 255

Leu Tyr Leu Phe Lys Trp Thr Thr Leu Leu Ile Pro Pro Thr Thr Leu
            260                 265                 270

Ile Ile Leu Asn Met Val Gly Val Val Ala Gly Val Ser Asp Ala Ile
        275                 280                 285

Asn Asn Gly Tyr Gly Ser Trp Gly Pro
    290                 295

<210> SEQ ID NO 9
<211> LENGTH: 298
<212> TYPE: PRT
<213> ORGANISM: Solanum lycopersicum

<400> SEQUENCE: 9

Met Pro Gln Ile Lys Leu Glu Lys Lys Phe Gly Gln Ser Pro Val Phe
  1               5                  10                  15

Val Ala Ser Thr Leu Leu Glu Asp Gly Gly Ile Pro Pro Gly Ala Thr
                 20                  25                  30

Ser Ala Ser Leu Leu Lys Glu Ala Ile His Val Ile Ser Cys Gly Tyr
             35                  40                  45

Glu Asp Lys Thr Glu Trp Gly Lys Glu Ile Gly Trp Ile Tyr Gly Ser
         50                  55                  60

Val Thr Glu Asp Ile Leu Thr Gly Phe Lys Met His Cys His Gly Trp
 65                  70                  75                  80

Arg Ser Val Tyr Cys Met Pro Asp Arg Pro Ala Phe Lys Gly Ser Ala
                 85                  90                  95

Pro Ile Asn Leu Ser Asp Arg Leu His Gln Val Leu Arg Trp Ala Leu
            100                 105                 110

Gly Ser Val Glu Ile Phe Phe Ser Arg His Cys Pro Ile Trp Tyr Gly
        115                 120                 125

Tyr Gly Cys Gly Leu Lys Pro Leu Glu Arg Phe Ser Tyr Ile Asn Ser
```

-continued

```
               130                 135                 140
Val Val Tyr Pro Leu Thr Ser Ile Pro Leu Ile Ile Tyr Cys Thr Leu
145             150                 155                 160

Pro Ala Val Phe Leu Leu Thr Arg Lys Phe Asn Trp Phe Pro Glu Ile
                165                 170                 175

Ser Asn Tyr Ala Ser Ile Leu Phe Met Gly Leu Phe Ile Met Ile Ala
                180                 185                 190

Val Thr Ser Val Ile Glu Met Gln Trp Gly Gly Val Ser Ile Asp Asp
                195                 200                 205

Trp Trp Arg Asn Glu Gln Phe Trp Val Ile Gly Gly Ala Ser Ser His
                210                 215                 220

Leu Phe Ala Leu Phe Gln Gly Leu Leu Lys Val Leu Ala Gly Val Asn
225                 230                 235                 240

Thr Ser Phe Thr Val Thr Ser Lys Ala Ala Asp Asp Gly Glu Phe Ser
                245                 250                 255

Glu Leu Tyr Leu Phe Lys Trp Thr Ser Leu Leu Ile Pro Pro Met Thr
                260                 265                 270

Leu Leu Ile Leu Asn Ile Ile Gly Val Val Val Gly Val Ser Asp Ala
                275                 280                 285

Ile Asn Asn Gly Tyr Asp Ser Trp Gly Pro
290                 295
```

PLANTS AND PLANT PRODUCTS USEFUL FOR BIOFUEL MANUFACTURE AND FEEDSTOCK, AND METHODS OF PRODUCING SAME

RELATED APPLICATIONS

This application claims priority from U.S. Provisional Application Ser. No. 61/097,361 filed Sep. 16, 2008, the entire disclosure of which is incorporated herein by this reference.

TECHNICAL FIELD

The presently disclosed subject matter relates to methods of selecting and/or producing plants having a beneficial saccharification properties. Plant cellulose or biomass obtained from plants having the beneficial saccharification properties can be more easily and efficiently converted to a useful bio fuel, and can be used as feedstock having improved digestibility.

INTRODUCTION

Plants use atmospheric carbon and sunlight during photosynthesis to produce their biomass (1), of which a majority is sugar polymers stored in the plant cell wall (2). Utilization of these sugar polymers is an attractive form of renewable energy, with particular interest in the production of alcohol from cellulosic biomass (2). Approximately 180 billion tons of cellulose are produced by plants per annum, forming the most abundant organic polymer on the planet (3). However, recalcitrance of cellulose to saccharification presents a major technical hurdle to overcome if cost-effective biochemical conversion of lignocellulosic biomass into bio fuels is to be realized.

Current best practices use costly chemical pretreatments to convert lignocellulo sic material to fermentable sugars (2). Along these lines, another potentially advantageous modification to the cell wall lies in changing the high-order crystalline structure of cellulose, which is formed of individual (1-4) linked β-D-glucosyl residues that coalesce via hydrogen bonding to form cellulose micro fibrils.

A defining feature of the plant cell is a rigid cell wall that constrains internal turgor pressure and yet must possess a degree of elasticity in order to allow the cell to grow and acquire shape (5). The central load bearing component of the cell wall is cellulose microfibrils, which are often highly organized with respect to growth pattern and cell shape (6). Synthesis of cellulose microfibrils occurs via a complex of plasma membrane-localized proteins containing several structurally similar cellulose synthase (CESA) subunits (6) that can be visualized as symmetrical rosettes of six globular complexes approximately 25-30 nm in diameter (FIG. 1D) (7). The only known components of the cellulose synthase complex in higher plants are the CESA proteins, 10 genes of which have been identified in the sequenced genome of *Arabidopsis thaliana* (7). The only known components of the cellulose synthase complex in higher plants are the CESA proteins (7).

Tight bonding capacity of the hydroxyl groups via hydrogen bonding are critical to determining how the crystal structure of cellulose forms and also in directing important physical properties of cellulose materials (8). It is postulated that the chains of glucosyl residues in the fibril periodically fail to coalesce into an ordered crystalline structure; these amorphous zones along the fibril length can possibly serve the association between hemicellulose and cellulose fibrils (5). Indeed, the regulation of amorphous to crystalline zones in the cellulose micro fibril and the potential for biological regulation has important connotations for plant design and cellulose bioconversion, but as yet this area of research is poorly understood.

Thus, there remains a need for increasing the availability of cellulose from plants for conversion into fermentable glucose for use in the production of ethanol and other biomass energy sources.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes a method of processing plant cellulose, which includes providing plant cellulose that is from a plant expressing a CESA polypeptide variant having at least one amino acid mutation in its carboxy-terminal transmembrane region, and saccharifying the plant cellulose to produce fermentable sugars. In some embodiments, the method also includes fermenting the fermentable sugars to produce alcohol.

In some embodiments, the CESA polypeptide variant is a CESA selected from: CESA-1 polypeptide variant, CESA-2 polypeptide variant, CESA-3 polypeptide variant, CESA-4 polypeptide variant, CESA-5 polypeptide variant, CESA-6 polypeptide variant, CESA-7 polypeptide variant, CESA-8 polypeptide variant, CESA-9 polypeptide variant, and CESA-10 polypeptide variant. In some embodiments, the CESA polypeptide variant is a CESA selected from: CESA-1 polypeptide variant, CESA-3 polypeptide variant, and CESA-6 polypeptide variant. In some embodiments, the CESA polypeptide variant is a CESA selected from: CESA-1 polypeptide variant and CESA-3 polypeptide variant. In some embodiments, the CESA polypeptide variant is CESA-1 polypeptide variant. In some embodiments, the CESA polypeptide variant is CESA-3 polypeptide variant.

In some embodiments, the CESA polypeptide variant includes at least one substitution at an amino acid from 840-1065 of the CESA polypeptide, where residue numbers 840-1065 refer to those residues of full-length wild type CESA polypeptide. In some embodiments, the CESA polypeptide variant includes at least one substitution at an amino acid from 900-1065. For example, in some embodiments, the at least one amino acid mutation includes a substitution at amino acid 942. In some embodiments, the at least one amino acid mutation includes a substitution at amino acid 942 from threonine to isoleucine. In some embodiments, the at least one amino acid mutation includes a substitution at amino acid 998. In some embodiments, the at least one amino acid mutation includes a substitution at amino acid 998 from glycine to aspartic acid. In some embodiments, the at least one amino acid mutation includes a substitution at amino acid 903. In some embodiments, the at least one amino acid mutation includes a substitution at amino acid 903 from alanine to valine. In some embodiments, the at least one amino acid mutation includes a substitution at amino acid 1064. In some embodiments, the at least one amino acid mutation includes a substitution at amino acid 1064 from arginine to tryptophan.

The plant cellulose from the plant expressing the CESA polypeptide variant has an measurable increase in saccharification efficiency relative to a wild type plant. In some embodiments, the plant cellulose has at least about a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, or more increase in saccharification efficiency relative to the wild type plant. In some embodiments, the plant cellulose has at least about a 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or more decrease in relative crystallinity relative to the wild type plant.

In some embodiments, the plant is a plant selected from: *Andropogon, Arabidopsis, Araucaria, Arundo, Aspidistra, Betula, Brachypodium, Chasmanthium, Cyanodon, Cynara, Eragrostis, Eucalyptus, Festuca, Miscanthus, Muhlenbergia, Nicotiana, Oryza, Panicum, Phalaris, Pinus, Pisum, Platanus, Podocarpus, Populus, Saccharum, Salix, Solanum, Sorghastrum, Sorghum, Spentina, Tripsacum*, and *Zea*.

The presently-disclosed subject matter includes a method of processing plant cellulose, which includes measuring a relative crystallinity index of plant cellulose, providing the plant cellulose if the relative crystallinity index is indicative of beneficial saccharification properties, and saccharifying the plant cellulose to produce fermentable sugars. In some embodiments, the method also includes fermenting the fermentable sugars to produce alcohol.

In some embodiments, the relative crystallinity index that is indicative of beneficial saccharification properties is about a 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or more decrease in relative crystallinity relative to the wild type plant.

In some embodiments, the a plant expresses a CESA polypeptide variant having at least one amino acid mutation in its carboxy-terminal transmembrane region.

The presently-disclosed subject matter includes a method of producing a plant having beneficial saccharification properties, which includes introducing into a plant a polynucleotide encoding a CESA polypeptide variant having at least one amino acid mutation in its carboxy-terminal transmembrane region, and expressing in the plant the CESA polypeptide variant, wherein the plant expressing the CESA polypeptide variant produces plant cellulose having beneficial saccharification properties as compared to plant cellulose produced by a wild-type plant.

In some embodiments, introducing the polynucleotide into the plant comprises transforming at least one cell of the plant with a heterologous polynucleotide encoding the CESA polypeptide variant. Such introduction can be accomplished by molecular biology methods know to those skilled in the art. In some embodiments, introducing the polynucleotide into the plant comprises applying a compound to a plant to create a mutation in the polynucleotide, such that the polypeptide encodes the CESA polypeptide variant having at least one amino acid mutation in its carboxy-terminal transmembrane region. In some embodiments, the compound is a herbicide to which the produced plant is resistant. In some embodiments, the compound is isoxaben. Such introduction can be accomplished using forward genetics and selection techniques known to those skilled in the art.

In some embodiments, the plant is a plant selected from: *Andropogon, Arabidopsis, Araucania, Arundo, Aspidistra, Betula, Brachypodium, Chasmanthium, Cyanodon, Cynara, Eragrostis, Eucalyptus, Festuca, Miscanthus, Muhlenbergia, Nicotiana, Oryza, Panicum, Phalaris, Pinus, Pisum, Platanus, Podocarpus, Populus, Saccharum, Salix, Solanum, Sorghastrum, Sorghum, Spentina, Tripsacum*, and *Zea*.

In some embodiments, the CESA polypeptide variant is a CESA selected from: CESA-1 polypeptide variant, CESA-2 polypeptide variant, CESA-3 polypeptide variant, CESA-4 polypeptide variant, CESA-5 polypeptide variant, CESA-6 polypeptide variant, CESA-7 polypeptide variant, CESA-8 polypeptide variant, CESA-9 polypeptide variant, and CESA-10 polypeptide variant. In some embodiments, the CESA polypeptide variant is a CESA selected from: CESA-1 polypeptide variant, CESA-3 polypeptide variant, and CESA-6 polypeptide variant. In some embodiments, the CESA polypeptide variant is a CESA selected from: CESA-1 polypeptide variant and CESA-3 polypeptide variant. In some embodiments, the CESA polypeptide variant is CESA-1 polypeptide variant. In some embodiments, the CESA polypeptide variant is CESA-3 polypeptide variant.

In some embodiments, the CESA polypeptide variant includes at least one substitution at an amino acid from 840-1065 of the CESA polypeptide, where residue numbers 840-1065 refer to those residues of full-length wild type CESA polypeptide. In some embodiments, the CESA polypeptide variant includes at least one substitution at an amino acid from 900-1065. For example, in some embodiments, the at least one amino acid mutation includes a substitution at amino acid 942. In some embodiments, the at least one amino acid mutation includes a substitution at amino acid 942 from threonine to isoleucine. In some embodiments, the at least one amino acid mutation includes a substitution at amino acid 998. In some embodiments, the at least one amino acid mutation includes a substitution at amino acid 998 from glycine to aspartic acid. In some embodiments, the at least one amino acid mutation includes a substitution at amino acid 903. In some embodiments, the at least one amino acid mutation includes a substitution at amino acid 903 from alanine to valine. In some embodiments, the at least one amino acid mutation includes a substitution at amino acid 1064. In some embodiments, the at least one amino acid mutation includes a substitution at amino acid 1064 from arginine to tryptophan.

The plant cellulose from the plant expressing the CESA polypeptide variant has an measurable increase in saccharification efficiency relative to a wild type plant. In some embodiments, the plant cellulose has at least about a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, or more increase in saccharification efficiency relative to the wild type plant. In some embodiments, the plant cellulose has at least about a 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or more decrease in relative crystallinity relative to the wild type plant.

The presently-disclosed subject matter includes a composition comprising plant cellulose having beneficial saccharification properties, wherein the plant cellulose is from a plant expressing a CESA polypeptide variant having at least one amino acid mutation in its carboxy-terminal transmembrane region. In some embodiments, the composition is used to produce a biofuel. In some embodiments, the composition is used as a feedstock.

The plant cellulose from the plant expressing the CESA polypeptide variant has an measurable increase in saccharification efficiency relative to a wild type plant. In some embodiments, the plant cellulose has at least about a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, or more increase in saccharification efficiency relative to the wild type plant. In some embodiments, the plant cellulose has at least about a 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or more decrease in relative crystallinity relative to the wild type plant.

BRIEF DESCRIPTION OF THE DRAWINGS

FIG. 1A includes a simplified version of the primary cell wall (PCW); FIG. 1B includes a depiction of the secondary cell wall (SCW); FIG. 1C includes a schematic of the production of cellulose having beneficial saccharification properties. FIG. 1D includes a molecular model of the CESA membrane rosette showing the molecular configuration of a single rosette subunit (left) and the complete CESA rosette (right).

FIG. 2 further shows various functional regions of the CESA protein and the interaction of the protein with the cell membrane.

FIG. 3 is a sequence alignment of CESA3 from *Arabidopsis* with CESA1 and CESA3 proteins from other plant species (SEQ ID NOS: 4-9). The alignment demonstrates the high level of conservation between different CESA as well as CESA3 across species, and in particular in the region of mutation determined relevant for reducing RCI. In particular, it is noted that threonine 942 is completely conserved across CESA proteins and species. It is predicted that T942 is a vital phosphorylation site and when changed to isoleucine (as disclosed herein—T942I) is non functional.

FIG. 5A shows analysis of various *Arabidopsis* plants carrying mutations in a number of genes critical to cellulose biosynthesis by hydrolytic enzyme saccharification efficiency. The graph plots fermentable sugars released relative to the conversion rate of wild type biomass as a percentage (n=3) FIG. 5B plots the relative crystallinity index (RCI) of the biomass sample measured by x-ray diffraction (n=3).

FIG. 10 includes schematic map of the plant expression constructs (pKM24-CESA3-1, pKM24-CESA3-2, pKM24-CESA3-3) with the chimeric CESA3 gene (GenBank accession no. NM120599).

BRIEF DESCRIPTION OF THE SEQUENCE LISTING

Figure 1:
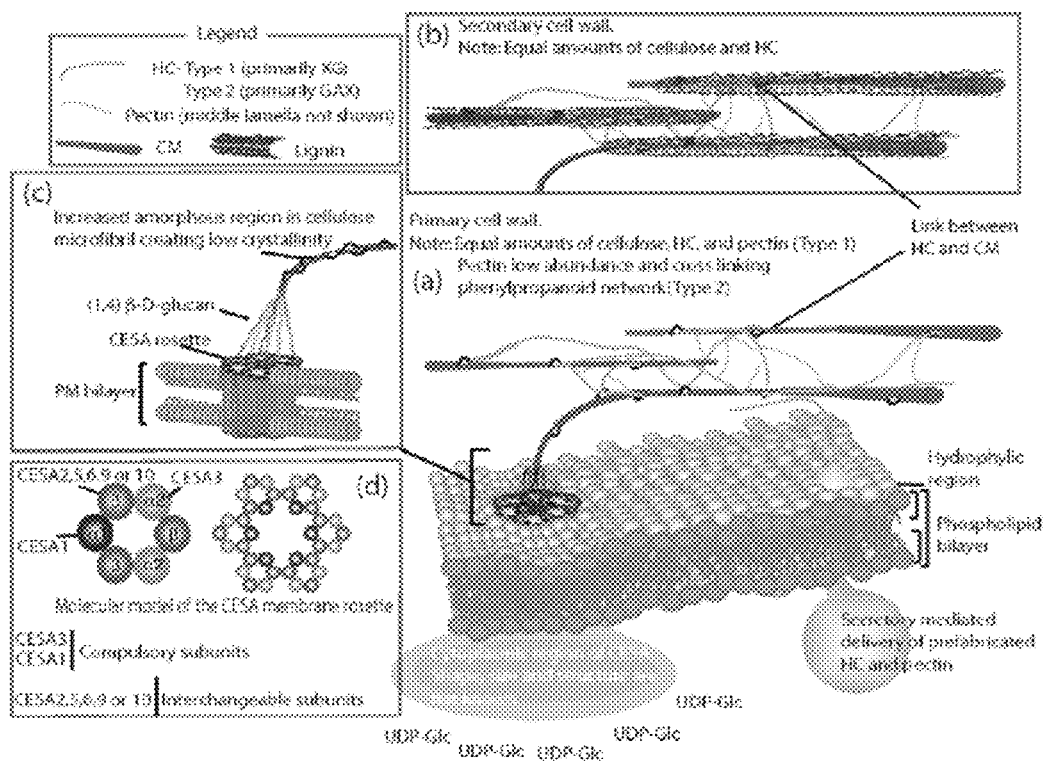
FIG. 1 includes a schematic representation of the general structure of the plant cell wall matrix with emphasis on cellulose.

SEQ ID NO: 1 is a wild type polynucleotide sequence encoding a CESA-3 polypeptide from *Arabidopsis thaliana*.

SEQ ID NO: 2 is a wild type polypeptide sequence of a CESA-3 polypeptide from *A. thaliana*.

SEQ ID NO: 3 polypeptide sequence of a CESA-3 polypeptide having a T942I mutation.

SEQ ID NO: 4 is a polypeptide sequence of a portion of a CESA-3 from *Betula pendula*, presented in alignment with other CESA polypeptides in FIG. 3.

SEQ ID NO: 5 is a polypeptide sequence of a portion of a CESA-3 from *Zea mays*, presented in alignment with other CESA polypeptides in FIG. 3.

SEQ ID NO: 6 is a polypeptide sequence of a portion of a CESA-3 from *Arabidopsis thaliana*, presented in alignment with other CESA polypeptides in FIG. 3.

SEQ ID NO: 7 is a polypeptide sequence of a portion of a CESA-1 from *Arabidopsis thaliana*, presented in alignment with other CESA polypeptides in FIG. 3.

SEQ ID NO: 8 is a polypeptide sequence of a portion of a CESA-3 from *Populus trichocarpa*, presented in alignment with other CESA polypeptides in FIG. 3.

SEQ ID NO: 9 is a polypeptide sequence of a portion of a CESA3 from *Solanum lycopersicum*, presented in alignment with other CESA polypeptides in FIG. 3.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes a method of processing plant cellulose, and a biofuel produced by the method of processing plant cellulose. The presently-disclosed subject matter further includes a method of producing a plant having beneficial saccharification properties, and a plant having beneficial saccharification properties. The presently-disclosed subject matter further includes a composition comprising plant cellulose having beneficial saccharification properties, which composition can be used to produce a bio fuel or as feedstock. Such feedstock can have improved digestibility and dietary efficiency in ruminants, e.g., cattle.

The basic steps of converting plant cellulose or biomass to a bio fuel include saccharifying the plant cellulose, and fermenting the sugars that are obtained from the saccharification of the cellulose. The conversion of plant cellulose to fermentable sugars is often referred to as saccharification or hydrolysis.

The term "biofuel", as used herein, refers to a fuel that is produced from plant material. Alcohol (e.g., ethanol) is an example of a biofuel.

"Plant cellulose" is a complex polysaccharide component of a plant that includes a plurality of bonded glucose units. As is well known, the glucose units of plant cellulose are typically connected through both glycosidic bonds within a single cellulose chain, and by hydrogen bonds within the chain or with adjacent cellulose chains, resulting in a strong crystalline structure.

The term "biomass", as used herein, refers to a plant product that comprises plant cellulose. As such, unless indications are made to the contrary, when methods herein are described as making use of plant cellulose, the description is inclusive of the methods making use of biomass, because biomass comprises plant cellulose. Similarly, unless indications are made to the contrary, when compositions herein are described as including plant cellulose, the description is inclusive of the compositions including biomass, because the biomass comprises plant cellulose.

"Saccharification" refers to the process of breaking a complex carbohydrate, such as cellulose, into its monosaccharide components. The monosaccharides or fermentable sugars can be utilized for fermentation and the production of ethanol, or for other biomass energy sources and uses (e.g., as forage materials). As noted herein, the intrinsic highly ordered and crystalline nature of cellulose makes it recalcitrant to saccharification.

One of the most challenging obstacles to overcome in finding an efficient and cost-effective method of producing bio fuels is the difficulty in efficiently saccharifying plant cellulose, which results from the molecular architecture of the cellulose polymers making up plant cell walls. Modifications to the processes of cellulose and cell wall biosynthesis in plants offer great potential for enhancing the ease of cellulosic conversion to fermentable sugars, increasing overall yields of released sugars, and decreasing overall conversion costs. However, the possibility of creating "flawed" or "wounded" cellulose better amenable to enzymatic hydrolysis by genetic means has been considered highly challenging to plant scientists. It has been noted in the literature that although changing the nature of cellulose to be more accessible to enzymatic hydrolysis would be of potential benefit, it was further noted that such a process would be very difficult and that it is uncertain whether such a plant would survive and thrive. (18).

The present inventors have surprisingly determined that beneficial saccharification properties can be conferred to cellulose of a plant, as will be further described herein.

In some embodiments, a method of producing a plant having beneficial saccharification properties includes introducing into a plant a polynucleotide encoding a CESA polypeptide variant having at least one amino acid mutation in its carboxy-terminal transmembrane region; and expressing in the plant the CESA polypeptide variant, wherein plant cellulose of the plant expressing the CESA polypeptide variant has beneficial saccharification properties as compared to a wild-type plant.

As used herein, the term "plant" includes reference to whole plants, plant parts or organs (e.g., leaves, stems, roots, etc.), plant cells, seeds and progeny of same. Plant cell, as used herein includes, without limitation, cells obtained from or found in: seeds, suspension cultures, embryos, meristematic regions, callus tissue, leaves, roots, shoots, gametophytes, sporophytes, pollen, and microspores. Plant cells can also be understood to include modified cells, such as protoplasts, obtained from the aforementioned tissues. The class of plants which can be used in the methods of the present subject matter is generally as broad as the class of higher plants comprising significant cellulosic materials, including both monocotyledonous and dicotyledonous plants. In some embodiments, a plant of interest is a plant selected from the group consisting of *Andropogon, Arabidopsis* (e.g., *Arabidopsis thaliana*), *Araucania, Arundo* (e.g., *Arundo donax*), *Aspidistra, Betula* (e.g., *Betula pendula*), *Brachypodium, Chasmanthium, Cyanodon, Cynara, Eragrostis, Eucalyptus, Festuca, Miscanthus, Muhlenbergia, Nicotiana, Oryza, Panicum* (e.g., *Panicum virgatum*), *Phalaris, Pinus, Pisum, Platanus, Podocarpus, Populus* (e.g., *Populus tremuloides, Populus trichocarpa*), *Saccharum, Salix, Solanum* (e.g., *Solanum lycopersicum*), *Sorghastrum, Sorghum, Spentina, Tripsacum* (e.g., *Tripsacum dactyloides*), and *Zea* (e.g., *Z. mays*). In some embodiments, the method of producing a plant having beneficial saccharification properties makes use of a plant selected from the group consisting of tree genus such as *Populus, Platanus, Pinus, Eucalyptus* and *Salix* spp. as well as grasses, of the family Poaceae, such as *Miscanthus, Tripsicum, Panicum, Zea*, and *Oryza*. The preferred plant species will embody ideal growth rates for bioenergy agriculture and pulp and paper production.

The terms "polynucleotide" and "nucleic acid" refers to deoxyribonucleotides or ribonucleotides and polymers thereof in either single or double stranded form. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed base and/or deoxyinosine residues (Batzer et al. (1991) Nucleic Acid Res 19:5081; Ohtsuka et al. (1985) J Biol Chem 260:2605 2608; Rossolini et al. (1994) Mol Cell Probes 8:91 98).

The terms "polypeptide," "protein," and "peptide," which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein," "polypeptide," and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

The term "variant" refers to an amino acid sequence that is different from the reference polypeptide by one or more amino acids. For example, in some embodiments, the amino acid sequence of the variant can differ by one or more amino acid mutations, including amino acid substitutions. For another example, in some embodiments, the amino acid sequence of the variant can differ by the insertion of one or more amino acids. For yet another example, in some embodiments the amino acid sequence of the variant can differ by the deletion of one or more amino acid sequences. As such, a "CESA polypeptide variant" is an amino acid sequence that differs from the reference polypeptide, CESA polypeptide, by one or more amino acids. As used herein, the term "mutation" means a change, inherited, naturally occurring, or introduced, in a nucleic acid or polypeptide sequence, including a change from one or more nucleic acids or amino acids in the wild type sequence to different one or more nucleic acids or amino acids in the variant; the insertion of one or more nucleic acids or amino acids into the wild type sequence, such that the variant includes one or more additional nucleic acids or amino acids relative to the wild type sequence; or the deletion of one or more nucleic acids or amino acids from the wild type sequence, such that the variant includes one or more fewer nucleic acids or amino acids relative to the wild type sequence.

A variant can also be a "functional variant," in which case the polypeptide is capable of affecting beneficial change in saccharification properties, e.g., increased saccharification efficiency. A functional variant of a wild-type reference polypeptide has an enhanced ability, relative to the reference polypeptide, to confer beneficial change in saccharification properties. As such, a CESA polypeptide variant that confers beneficial saccharification properties to cellulose of a plant, as compared to a wild type CESA polypeptide, is a functional variant. In this regard, for a CESA polypeptide variant that differs from the reference polypeptide by the insertion of one or more amino acids ("insertion variant"), the number of amino acids that can be inserted can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30. A functional variant can further include conservatively substituted variants. The term "conservatively substituted variant" refers to a polypeptide comprising an amino acid residue sequence that differs from a reference polypeptide by one or more conservative amino acid substitutions, and exhibits beneficial saccharification properties. The phrase "conservatively substituted variant" also includes polypeptides wherein a residue is replaced with a chemically derivatized residue, provided that the resulting polypeptide is capable of affecting an increase in saccharification efficiency.

A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another such as between arginine and lysine, between glutamine and asparagine, between threonine and serine; the substitution of one basic residue such as lysine or arginine for another; the substitution of one acidic residue, such as aspartic acid or glutamic acid for another; or the substitution of one aromatic residue, such as phenylalanine, tyrosine, or tryptophan for another.

Conversely, a "non-conservative amino acid substitution" is a substitution of an amino acid residue with a functionally dissimilar residue. For example, a nonconservative substitution includes the substitution of a non-polar (hydrophobic) residue such as isoleucine, valine, leucine, or methionine, with a charged or polar (hydrophilic) residue such as arginine, lysine, glutamine, asparagine, threonine, or serine.

By way of providing an example with regard to non-conservative amino acid substitutions, in some embodiments, a CESA polypeptide variant includes a mutation from threonine to isoleucine. The CESA polypeptide variant can be described as including a mutation that involves a non-conservative amino acid substitution, because threonine, which is generally hydrophilic, can be described as functionally dissimilar from isoleucine, which is generally hydrophobic. For anther example, a CESA polypeptide variant including a mutation from glycine to aspartic acid can be described as including a mutation that involves a non-conservative amino acid substitution, because glycine, which is generally nonpolar, can be described as functionally dissimilar from aspartic acid, which is charged. For anther example, a CESA polypeptide variant including a mutation from arginine to tryptophan can be described as including a mutation that involves a non-conservative amino acid substitution, because arginine, which is generally polar, can be described as functionally dissimilar from tryptophan, which is nonpolar and aromatic.

By way of providing an example with regard to conservative amino acid substitutions, a conservatively substituted variant of a CESA polypeptide variant having a mutation from threonine to isoleucine could be a CESA polypeptide variant having a mutation from threonine to valine, because isoleucine and valine are functionally similar.

The terms "polypeptide fragment" or "fragment," when used in reference to a polypeptide, refers to a polypeptide in which amino acid residues are deleted as compared to the reference polypeptide itself, but where the remaining amino acid sequence is usually identical to the corresponding positions in the reference polypeptide, such as for example a native polypeptide. Such deletions can occur at the amino-terminus or carboxy-terminus of the reference polypeptide, or alternatively both. Such deletions can also occur at a location within the polypeptide that is between the amino-terminus and carboxy-terminus. Fragments typically are at least about 50, 60, 70, 80, 90, 100, 110, 120, 130, 140, 150, 160, 170, 180, 190, 200, 225, 250, or 275 amino acids long. A fragment of a reference polypeptide also refers to a fragment of a variant of the reference polypeptide, for example, a variant wherein one or more amino acid residues are deleted as compared to the variant. A fragment can also be a "functional fragment," meaning that the fragment is capable of conferring beneficial saccharification properties to plant cellulose of a plant.

As used herein, "CESA" polypeptide refers to the catalytic subunits of a plant cellulose synthase enzyme complex. With reference to FIG. 1, and particularly with reference to FIG. 1D, Cellulose is synthesized in higher plants via a multimeric plasma membrane-localized complex that can be visualized as symmetrical rosettes of six globular complexes approximately 25-30 nm in diameter. Further, it is appreciated that plants contain multiple CESA proteins. For example, the CESA gene family in *Arabidopsis* contains 10 family members, termed CESA-1 to CESA-10, and each shows different patterns of expression and different functional characteristics.

Reference is made to FIG. 1, which includes a schematic representation of the general structure of the plant cell wall matrix with emphasis on cellulose. FIG. 1A provides a simplified version of the primary cell wall (PCW), shown as a network of cellulose microfibrils (CM) interlocked and coated by cross-linking hemicelluloses (HC), which are primarily xyloglucans (XG) in Type I walls and glucuronoarabinoxylans (GAX) in Type II walls. Together, CMs and HCs are embedded in a matrix of pectin (Type I) or acidic polysaccharides (Type II) with various levels of proteins (not shown) that aid in wall structure, assembly and degradation (Vergara and Carpita, 2001). Cellulose is being synthesized at the plasma membrane (PM) by a symmetrical rosette of six globular cellulose synthase (CESA) protein complexes (Brown, 1996, Herth, 1983). The CESA rosette incorporates UDP-glucose molecules, present in the cytosol, into growing β-1,4-linked glucan chains, a total of 36 of which are produced by a single rosette which then cocrystallize to form a single microfibril (Herth, 1983). Occasionally, the glucan chains are thought to form less ordered regions that structurally form amorphous zones along the length of the CM, rather than crystalline regions (O'Sullivan, 1997), which may serve as specific connection points between the cross-linking HCs and the CM (Himmel et al., 2007). The precise architecture of the CESA rosette complex and the identity of possible proteins with which it interacts at the cytosolic and extracellular PM surface have yet to be resolved. For this reason, and because most of the proteins, including the catalytic domains, extend into the cytoplasm, the CESA complex is depicted as a nebulous, ill-defined structure in the cytosol. HCs and pectin are shown being delivered, prefabricated, to the cell wall matrix through the PM via a Golgi secretory vesicle.

Turning now to FIG. 1B, the secondary cell wall (SCW) is produced by certain cell types as part of the maturation process after growth has ceased and consists primarily of CMs, HCs and lignin. Lignification results in the coating of CMs with anhydrous lignin polymers that further strengthen the cell wall but also present a major barrier in the bioconversion process to biofuels by blocking access and causing adsorption of hydrolytic enzymes (Moiser et al., 2005).

FIG. 1C includes a schematic of the production of cellulose having beneficial saccharification properties. Cellulose crystallinity is another important factor contributing to the recalcitrant nature of most lignocellulosic biomass to enzymatic degradation (Moiser et al., 2005). Genetic modification of various CESA proteins has been shown to reduce the crystallinity of the lignocellulosic biomass and enhance enzymatic degradation (Harris et al., 2009). Without wishing to be bound by theory or mechanism, this phenomenon could occur through the creation of more amorphous regions within the cellulose microfibril or by causing a proportional shift in the volume fraction of the cell wall between the cellulose, hemicellulose and lignin fractions. Here the glucan chains produced by the different CESA protein are color coordinated to match FIG. 1D.

FIG. 1D includes a molecular model of the CESA membrane rosette showing the molecular configuration of a single rosette subunit (left) and the complete CESA rosette (right). Each rosette subunit is identical, consisting of one molecule of α1, two molecules of α2 and three molecules of β type CESA proteins (Ding and Himmel, 2006). Only three possible types of protein-protein interactions are necessary (α1-β, α2-β, and β-β) for rosette assembly in the plasma membrane or for rosette-rosette interaction to constitute the array formation seen in the parenchyma cells of maize stem pith (not shown) (Ding and Himmel, 2006). Interchangeable versus compulsory CESA subunits in the primary cell wall CESA complex are defined as CESA1 and CESA3 are compulsory and CESA 2, 5, 7, 9, and 10 are interchangeable. For the secondary cell wall CESA complex CESA4, 7 and 8 are all necessary components for correct secondary cell wall cellulose synthesis. Figure not to scale (adapted from Harris and DeBolt, 2009 Plant Biotechnology Journal).

Figure 4:
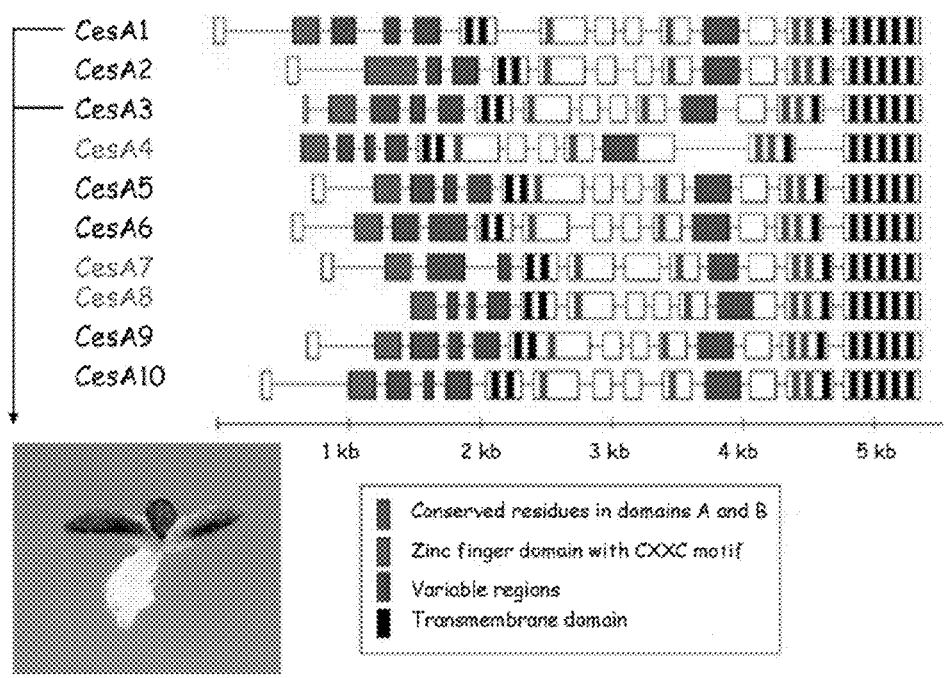
FIG. 4 is a schematic drawing showing alignment of the different family members of *Arabidopsis* CESA family members at functional domains. Note in particular the high degree of functional homology at the carboxy-terminal transmembrane domain.

With reference to FIG. 4, each of these CESA polypeptides exhibit high homology to one another, particularly with the carboxy-terminal transmembrane region. In some embodiments, the method of producing a plant having beneficial saccharification properties includes expressing a CESA polypeptide variant selected from the group consisting of: CESA-1 polypeptide variant, CESA-2 polypeptide variant, CESA-3 polypeptide variant, CESA-4 polypeptide variant, CESA-5 polypeptide variant, CESA-6 polypeptide variant, CESA-7 polypeptide variant, CESA-8 polypeptide variant, CESA-9 polypeptide variant, and CESA-10 polypeptide variant. In some embodiments, the method of producing a plant having beneficial saccharification properties includes expressing a CESA polypeptide variant selected from the group consisting of: CESA-1 polypeptide variant, CESA-3 polypeptide variant, CESA-6 polypeptide variant. In some embodiments, the method of producing a plant having beneficial saccharification properties includes expressing a CESA polypeptide variant selected from the group consisting of: CESA-1 polypeptide variant and CESA-3 polypeptide variant. In some embodiments, a plant having beneficial saccharification properties includes expressing more than one CESA polypeptide variant. For example, in some embodiments, a plant having beneficial saccharification properties can express a CESA-3 polypeptide variant and a CESA-1 polypeptide variant.

In some embodiments, the method of producing a plant having beneficial saccharification properties includes expressing a CESA polypeptide variant having at least one amino acid mutation in its carboxy-terminal transmembrane region, wherein the carboxy-terminal transmembrane region refers to amino acids 840-1065 of a full length wild-type CESA polypeptide. In some embodiments, the carboxy-terminal transmembrane region of a CESA polypeptide refers to amino acids 900-1065.

Using CESA-3 (SEQ ID NO: 2) as an initial example, amino acids 840-1065 can be identified as the carboxy-terminal transmembrane region of CESA-3, the same region in any other CESA polypeptide can be selected as the carboxy-terminal transmembrane region. Indeed, the identified residues of 840-1065 in CESA-3 would translate into the other CESA polypeptides, with additions or subtractions of less than fifteen, less than ten, less than five, less than two, or no residues, because of the high conservation between CESA polypeptides in the, particularly in the carboxy-terminal transmembrane region. For example, the 840-1065 region of CESA-3 is equivalent to the 840-1065 region of CESA-1. For another example, the 840-1065 region of CESA-3 is equivalent to the 840-1065 region of CESA-6. As such, when amino acids 840-1065, for example, are identified as the carboxy-terminal transmembrane region, this identification is relevant to any CESA polypeptide, including CESA-1, CESA-2, CESA-3, CESA-4, CESA-5, CESA-6, CESA-7, CESA-8, CESA-9, and CESA-10.

Further, CESA polypeptides are highly conserved at the C-terminal transmembrane region across plant species and therefore gene and protein orthologs from other plant species are intended to be included in the presently-disclosed subject matter. As such, identified residues of 840-1065, for example, in a CESA polypeptide of one plant would translate into the CESA polypeptides of other plants, with additions or subtractions of less than fifteen, less than ten, less than five, less than two, or no residues, because of the high conservation between CESA polypeptides in the, particularly in the carboxy-terminal transmembrane region. For another example, identified residues of 840-1065 in a CESA-3 of one plant would translate into the CESA-3 of other plant species. For another example, identified residues of 840-1065 in a CESA-1 or CESA-3 of one plant would translate into the CESA-1 or CESA-3 of other plant species. For example, when amino acids 840-1065 are identified as the carboxy-terminal transmembrane region, this identification refers to a CESA polypeptide of any plant species, including, but not limited to *Arabidopsis, Betula, Cynara, Zea, Solanum, Nicotiana, Populus, Panicum, Podocarpus, Araucaria, Aspidistra, Pisum, Arundo donax, Miscanthus, Cyanodon, Phalaris, Eragrostis, Tripsacum dactyloides, Platanus, Pinus, Platanus, Festuca, Spentina, Saccharum, Eucalyptus, Chasmanthium, Sorghastrum, Muhlenbergia, Salix, Andropogon, Brachypodium, Oryza,* and *Sorghum*. FIG. 3 exemplifies the homology of CESA polypeptides between plant species, showing a sequence alignment demonstrating high sequence identity across polypeptide sequences in the CESA carboxy-terminal transmembrane region. Thus, when a CESA polypeptide is referenced herein, it is intended that all known CESA polypeptides are includes in the reference, across plant species and when a particular CESA polypeptide subunit (e.g., CESA-3) is referenced, it is intended that all known CESA-3 polypeptides across plant species are included in the reference.

Figure 2:
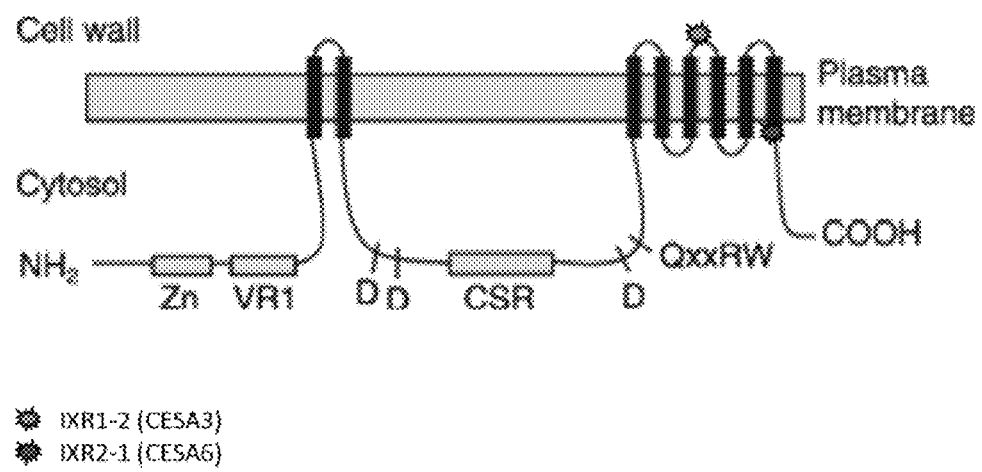
FIG. 2 is a schematic drawing of a CESA protein showing mutations effecting RCI and saccharification efficiency within the carboxy-terminal transmembrane domain of the CESA.

With reference to FIG. 2, in some embodiments, the methods comprise introducing into a plant a polynucleotide encoding a CESA polypeptide variant having at least one amino acid mutation within a carboxy-terminal transmembrane region of the CESA. In some embodiments, the CESA polypeptide variant includes two or more amino acid mutations within a carboxy-terminal transmembrane region of the CESA. In some embodiments, the at least one mutation can be an amino acid substitution at a residue within the carboxy-terminal transmembrane region, for example, an amino acid substation at amino acid within the carboxy-terminal transmembrane region selected from the following amino acids as identified by residue number of a full-length wild type CESA polypeptide: 1065, 1064, 1063, 1062, 1061, 1060, 1059, 1058, 157, 1056, 1055, 1054, 1053, 1052, 1051, 1050, 1049, 1048, 1047, 1046, 1045, 1044, 1043, 1042, 1041, 1040, 1039, 1038, 1037, 1036, 1035, 1034, 1033, 1032, 1031, 1030, 1029, 1028, 1027, 1026, 1025, 1024, 1023, 1022, 1021, 1020, 1019, 1018, 1017, 1016, 1015, 1014, 1013, 1012, 1011, 1010, 1009, 1008, 1007, 1006, 1005, 1004, 1003, 1002, 1001, 1000, 999, 998, 997, 996, 995, 994, 993, 992, 991, 990, 989, 988, 987, 986, 985, 984, 983, 982, 981, 980, 979, 978, 977, 976, 975, 974, 973, 972, 971, 970, 969, 968, 967, 966, 965, 964, 963, 962, 961, 960, 959, 958, 957, 956, 955, 954, 953, 952, 951, 950, 949, 948, 947, 946, 945, 944, 943, 942, 941, 940, 939, 938, 937, 936, 935, 934, 933, 932, 931, 930, 929, 928, 927, 926, 925, 924, 923, 922, 921, 920, 919, 918, 917, 916, 915, 914, 913, 912, 911, 910, 909, 908, 907, 906, 905, 904, 903, 902, 901, 900, 899, 898, 897, 896, 895, 894, 893, 892, 891, 890, 889, 888, 887, 886, 885, 884, 883, 882, 881, 880, 879, 878, 877, 876, 875, 874, 873, 872, 871, 870, 869, 868, 867, 866, 865, 864, 863, 862, 861, 860, 859, 858, 857, 856, 855, 854, 853, 852, 851, 850, 849, 848, 847, 846, 845, 844, 843, 842, 841, and 840.

In some embodiments, the at least one mutation can be a non-conservative amino acid substitution. In some embodiments, the at least one mutation can be a conservative amino acid substitution.

In some embodiments, CESA polypeptide variant includes an amino acid substitution at amino acid 942. In some embodiments, CESA polypeptide variant includes a substitution at amino acid 942 from threonine to an amino acid selected from the group consisting of: isoleucine, valine, leucine, and methionine. In some embodiments, CESA polypeptide variant includes a substitution at amino acid 942 from threonine to isoleucine, i.e., T942I, (SEQ ID NO: 3).

In some embodiments, CESA polypeptide variant includes an amino acid substitution at amino acid 998. In some embodiments, CESA polypeptide variant includes a substitution at amino acid 998 from glycine to an amino acid selected from the group consisting of: aspartic acid and glutamic acid. In some embodiments, CESA polypeptide variant includes a substitution at amino acid 998 from glycine to aspartic acid, i.e., G998D.

In some embodiments, CESA polypeptide variant includes an amino acid substitution at amino acid 903. In some embodiments, CESA polypeptide variant includes a substitution at amino acid 903 from alanine to an amino acid selected from the group consisting of: valine, isoleucine, leucine, and methionine. In some embodiments, CESA polypeptide variant includes a substitution at amino acid 903 from alanine to valine, i.e., A903V.

In some embodiments, CESA polypeptide variant includes an amino acid substitution at amino acid 1064. In some embodiments, CESA polypeptide variant includes a substitution at amino acid 1064 from arginine to an amino acid selected from the group consisting of: tryptophan, phenylalanine, and tyrosine. In some embodiments, CESA polypeptide variant includes a substitution at amino acid 1064 from arginine to tryptophan, i.e., R1064W.

In some embodiments, the CESA polypeptide variant is a CESA-3 variant including a substitution at amino acid 942 from threonine to isoleucine. In some embodiments, the CESA polypeptide variant is a CESA-3 variant including a substitution at amino acid 998 from glycine to aspartic acid. In some embodiments, the CESA polypeptide variant is a CESA-1 variant including a substitution at amino acid 903 from alanine to valine. In some embodiments, the CESA polypeptide variant is a CESA-6 variant including a substitution at amino acid 1064 from arginine to tryptophan.

Creating various mutation variations envisioned by the presently-disclosed subject matter can be accomplished by a variety of protocols known in the art including those described in U.S. Pat. No. 6,448,048 issued to Tomono et al., on Sep. 20, 2002, which is incorporated herein by reference in its entirety.

As will be understood by those skilled in the art, introducing into a plant a polynucleotide encoding a CESA polypeptide variant, and expressing the CESA polypeptide variant can be accomplished using standard molecular biology techniques.

In some embodiments, "introducing" the polynucleotide into the plant comprises transforming at least one cell of the plant with a heterologous polynucleotide the polynucleotide encoding the CESA polypeptide variant.

The terms "heterologous", "recombinant", and "exogenous", when used herein to refer to a nucleic acid sequence (e.g., a DNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found. Similarly, when used in the context of a polypeptide or amino acid sequence, an exogenous polypeptide or amino acid sequence is a polypeptide or amino acid sequence that originates from a source foreign to the particular host cell or, if from the same source, is modified from its original form. Thus, exogenous DNA segments can be expressed to yield exogenous polypeptides. In contrast, a "homologous" nucleic acid (or amino acid) sequence is a nucleic acid (or amino acid) sequence naturally associated with a host cell into which it is introduced.

The terms "associated with", "operably linked", and "operatively linked" refer to two nucleic acid sequences that are related physically or functionally. For example, a promoter or regulatory DNA sequence is said to be "operatively linked with" a DNA sequence that encodes an RNA or a polypeptide if the two sequences are operatively linked, or situated such that the regulator DNA sequence will affect the expression level of the coding or structural DNA sequence.

With plant cells, a heterologous polynucleotide, e.g. a polynucleotide encoding a CESA polypeptide variant, can be introduced into a plant cell nucleus by methods known to those of ordinary skill in the art including, but not limited to, methods such as micropipette injection, electroporation, polyethylene glycol (PEG) mediated transformation of protoplasts, and gene gun or particle bombardment techniques.

Further, directed genetic modification and expression of heterologous polynucleotides in plants such as *Arabidopsis*, tobacco, etc. can be accomplished by using the T-DNA of the Ti plasmid of *Agrobacterium tumefaciens*. Following genetically engineered insertion of a foreign DNA fragment into T-DNA in *Agrobacterium*, the host plant can be transfected by the bacterium or Ti plasmid, thus inserting the foreign DNA into the host plant chromosome to eventually produce a genetically engineered plant. Alternatively Ri, or root-inducing, plasmids may be used as the gene vectors. Although *Agrobacterium* effectively transform only dicots, the Ti plasmid permits the efficacious manipulation of the bacteria to act as vectors in monocotyledonous crop plants, i.e., wheat, barley, rice, rye, etc. Alternatively, Ti plasmids or other plasmids can be introduced into monocots by artificial methods such as microinjection, or fusion between the monocot protoplasts and bacterial spheroplasts containing the T-region which could then be integrated into the plant nuclear DNA.

As such, a plant cell of the presently-disclosed subject matter can be, for example, a transformed plant cell. The terms "transformed", "transgenic", and "recombinant" refer to a cell, such as a plant cell, into which a heterologous nucleic acid molecule has been introduced. The nucleic acid molecule can be stably integrated into the genome of the cell, and/or the nucleic acid molecule can be present as an extrachromosomal molecule (e.g., a plasmid). Such an extrachromosomal molecule can be auto-replicating. Transformed cells are understood to encompass not only the end product of a transformation process, but also transgenic progeny thereof. A "non-transformed", "non-transgenic", or "non-recombinant" host refers to a wild type organism, e.g., a cell, which does not contain the heterologous nucleic acid molecule. For example, in some embodiments, the cell has been transformed with a plasmid comprising a heterologous expression cassette comprising a promoter operatively linked to a gene encoding the CESA polypeptide variant.

The term "expression cassette" refers to a nucleic acid molecule capable of directing expression of a particular nucleotide sequence in an appropriate host cell, comprising a promoter and/or other regulatory sequences operatively linked to the nucleotide sequence of interest which can be operatively linked to termination signals. It also typically comprises sequences required for proper translation of the nucleotide sequence. The coding region usually encodes a polypeptide of interest but can also encode a functional RNA of interest. The reporter gene cassette comprising the nucleotide sequence of interest can be chimeric, meaning that at least one of its components is heterologous with respect to at least one of its other components. The reporter gene cassette can also be one that is naturally occurring but has been obtained in a recombinant form useful for heterologous expression.

Typically, however, the reporter gene cassette is heterologous with respect to the host; i.e., the particular DNA sequence of the reporter gene cassette does not occur naturally in the host cell and was introduced into the host cell or an ancestor of the host cell by a transformation event. The expression of the nucleotide sequence in the reporter gene cassette can be under the control of a constitutive promoter or of an inducible promoter that initiates transcription only when the host cell is exposed to some particular external stimulus.

The term "gene" is used broadly to refer to any segment of DNA associated with a biological function. Thus, genes include, but are not limited to, coding sequences and/or the regulatory sequences required for their expression. Genes can also include non-expressed DNA segments that, for example, form recognition sequences for a polypeptide. Genes can be obtained from a variety of sources, including cloning from a source of interest or synthesizing from known or predicted sequence information, and can include sequences designed to have desired parameters.

In some embodiments, "introducing" the polynucleotide into the plant and "expressing" the polypeptide in the plant comprises making use of forward genetics and selection techniques, which will be known to those skilled in the art. Briefly, plants containing mutations are provided, and a compound (e.g., a herbicide) is applied to the plant. Mutant plants with resistance to the herbicide are isolated and the mutation is cloned such that it can be identified. When a particular type of mutation in a plant is known to be resistant to a particular compound (herbicide) such a plant can be isolated from a plurality of plants by applying that compound to the plants and isolating the compound-resistant plant. For example, certain plants expressing a CESA polypeptide variant having a mutation in its carboxy-terminal transmembrane region have been found to be resistant to the herbicide, isoxaben, as is described further in the Examples section. It is noted that, if a plant expressing a particular CESA polypeptide variant is resistant to a particular herbicide, it will be resistant to that herbicide regardless of whether the "introducing" of the polynucleotide and the "expressing" of the CESA polypeptide variant was affected by forward genetics techniques or transformation techniques. It is contemplated that introduction and expression of the desired CESA polypeptide variant can be accomplished by any method capable of accomplishing the desired introduction and expression, including forward chemical genetics or transgenic approaches.

As noted herein, the present inventors surprisingly discovered that cellulose from a plant expressing a CESA polypeptide variant having at least one amino acid mutation in its carboxy-terminal transmembrane region has beneficial saccharification properties. Beneficial saccharification properties refer to properties of a plant or cellulose produced from a plant, and particularly, the availability of cellulose from a plant for conversion into fermentable sugars (i.e., saccharification). Determination of whether a particular plant, or particular plant cellulose, has beneficial saccharification properties can be accomplished using various methods, including: saccharification efficiency analysis, relative crystallinity index analysis, and even high energy synchrotron source analysis.

Saccharification efficiency can be measured as a function of an amount of fermentable sugar (e.g., glucose) released from a cellulose sample exposed to one or more enzymes (e.g., cellulases) for a determined time period relative to the weight of the sample (%) and as compared to a wild-type control plant. Standardized enzymatic saccharification protocols are well known to those of ordinary skill in the art. One exemplary standardized enzymatic saccharification analytical protocol is provided by the National Renewable Energy Laboratory (LAP-009), which is incorporated herein by reference. However, the particular saccharification protocol is not a controlling factor, as the test cellulose is compared to a wild-type plant control cellulose sample analyzed using an identical saccharification protocol. In some embodiments, saccharification efficiency is expressed as a % increase, calculated using the following formula: % increase=$((t-w)/w)$ 100, where t is rate of release for the test plant, and w is rate of release for the wild type plant. In some embodiments, a measurable increase in saccharification efficiency for a test plant, relative to a wild type plant, is indicative of beneficial saccharification properties of the test plant and the plant cellulose derived therefrom. In some embodiments, a measurable increase in saccharification efficiency is indicative of beneficial saccharification properties. In some embodiments, an increase in saccharification efficiency of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, or more is indicative of beneficial saccharification properties. An exemplary saccarification efficiency analysis is described in the Examples section.

"Relative crystallinity index" or "RCI" as the terms are used herein refer to a relative structural measure of the size, density, absolute crystallinity, and/or orientation of cellulose in a plant, and in particular, cellulose microfibrils in a plant. As set forth in detail in the Examples, RCI can be measured using x-ray scattering analysis to measure an x-ray diffraction pattern of a sample of cellulose from a plant and measure any changes in the orientation, size, or density of the studied cellulose crystallites. The x-ray scattering analysis can be performed as set forth in Harris & DeBolt (2008) (13), which is incorporated herein by reference in its entirety. Briefly, in one exemplary procedure, a diffractometer can be used to measure x-ray diffraction with Cu K$\alpha$ radiation generated at about 30 mA and about 40 kV. Samples can be analyzed and compared to wild-type control samples to determine the RCI. Other procedures can be utilized if desired to measure RCI, and the present subject matter is not intended to be limited to measurement of RCI by x-ray scattering analysis. For example, RCI or elements thereof can also be determined for a cellulose sample by measuring transmission geometries using a similar x-ray diffractometer as set forth in Andersson et al., 2004 (18) or using a synchrotron x-ray and neutron fiber diffraction analysis as described by Nishimaya et al., 2002 (19).

Without wishing to be bound by theory or mechanism, it is believed that the CESA polypeptide variants described herein are incorporated into the plant cellulose synthase enzyme complex to produce cellulose that is "flawed" or "wounded," as compared to cellulose produced by a wild type plant. In other words, it is believed that plants expressing the CESA polypeptide variants produce cellulose having an altered structure with reduced cellulosic crystallinity, from which glucose can be more readily released. In this regard, RCI can be correlated to saccharification efficiency. A decrease in RCI of a test plant (as compared to a wild-type plant), correlates with increased saccharification efficiency.

In this regard, in some embodiments of the presently disclosed subject matter, a method of processing plant cellulose comprises, measuring the RCI of plant cellulose, providing the plant cellulose if the RCI is indicative of beneficial saccharification properties, and saccharifying the plant cellulose to produce fermentable sugars. In some embodiments the method can further include fermenting the fermentable sugars to produce alcohol.

In some embodiments, a measurable decrease in RCI for a test plant, relative to a wild type plant, is indicative of beneficial saccharification properties of the test plant and the plant cellulose derived therefrom. In some embodiments, a decrease in RCI of about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or more is indicative of beneficial saccharification properties. An exemplary x-ray scattering analysis is described in the Examples section.

The presently-disclosed subject matter includes a method of processing plant cellulose, and a biofuel produced by the method of processing plant cellulose. In some embodiments, the method of processing plant cellulose, includes providing plant cellulose that is from a plant expressing a CESA polypeptide variant having at least one amino acid mutation in its carboxy-terminal transmembrane region; and saccharifying the plant cellulose or biomass to produce fermentable sugars. In some embodiments, the provided plant cellulose is from a plant having beneficial saccharification properties as produced by methods of the presently-disclosed subject matter, described herein. In some embodiments, the method also includes fermenting the fermentable sugars to produce alcohol, which can be used as a bio fuel.

When the term "providing" is used in connection with providing plant cellulose for a method described herein, it is understood to include providing the plant cellulose by directly obtaining it from a plant (e.g., as in the case of a farmer or grower), as well as providing plant cellulose obtained from a third party (e.g., as in the case of a biofuel manufacturer). Additional information about biofuel, e.g., ethanol manufacturing using plants, can be found in Harris D & DeBolt S, 2009, "Synthesis, regulation and utilization of lignocellulosic biomass." *Plant Biotechnology Journal*, in press, which is incorporated herein by this reference.

The presently-disclosed subject matter includes a composition comprising plant cellulose having beneficial saccharification properties. In some embodiments, the plant cellulose has a measurable increase in saccharification efficiency as compared to a control. In some embodiments, the plant cellulose has a saccharification efficiency of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, or more % increase as compared to a control. The control plant cellulose can be derived from a plant having catalytic subunits of a plant cellulose synthase enzyme complex (CESA subunits) with wild type amino acid sequences in their carboxy-terminal transmembrane region. In some embodiments, the plant cellulose has an RCI that is lower, relative to a control, by about 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, or 10%.

In some embodiments, the plant cellulose is from a plant expressing a CESA polypeptide variant having at least one amino acid mutation in its carboxy-terminal transmembrane region. In some embodiments, the plant cellulose is from a plant having beneficial saccharification properties as produced by methods of the presently-disclosed subject matter, described herein. If desired, a sample of the plant cellulose can be tested to determine whether it is from a plant expressing a CESA polypeptide variant. For example, nucleotide sequence analysis of all the CESA genes within the host plant of interest would reveal any variations from the native CESA polypeptide sequence' in other words, such analysis could be used to determine whether the plant expresses a CESA polypeptide variant having at least one amino acid mutation in its carboxy-terminal transmembrane region.

The composition comprising plant cellulose of the presently-disclosed subject matter can be used to manufacture a biofuel (e.g., ethanol). In some embodiments, the composition comprising plant cellulose can be used to manufacture a bio fuel in accordance with the method of processing plant cellulose, described herein. The composition can also be used as feedstock. The term "feedstock", as used herein, refers to a plant product that comprises plant cellulose and is used for the purpose of providing nourishment to animals. Such feedstock can have improved digestibility and dietary efficiency in ruminants, e.g., cattle, due to its beneficial saccharification properties. The terms biomass and feedstock can refer to the same composition; however, when the term feedstock is used, a particular use is contemplated.

The presently-disclosed subject matter is further illustrated by the following specific but non-limiting examples. The following examples may include compilations of data that are representative of data gathered at various times during the course of development and experimentation related to the present invention.

EXAMPLES

The present inventors performed screens on a range of plants including mutation in CESA polypeptides. Firstly, the inventors screened for altered crystallinity arising from the cellulose in plant biomass using x-ray scattering. Secondly, the inventors screened for enzymatic conversion efficiency (also referred to herein as saccharification efficiency) of cellulosic biomass into fermentable sugars. Thirdly, for certain of the plants, the inventors were able to obtain additional data from Cornell University's high energy synchrotron source (CHESS).

The present inventors have discovered that the level of crystallinity of cellulose in plants (referred to as the Relative Crystallinity Index (RCI)) affects availability of the cellulose for enzymatic hydrolysis to simple sugars. Thus, by genetic manipulation of plant CESA enzymes and selection of mutants with reduced RCI as compared to wild type, plants with increased saccharification efficiency have been produced.

The inventors surprisingly discovered that beneficial saccharification properties can be conferred to cellulose from a plant expressing a CESA polypeptide variant including at least one mutation in the carboxy-terminal transmembrane region (Table 1), while such beneficial properties are not conferred to cellulose from plants expressing a CESA polypeptide variant including a mutation in regions outside the carboxy-terminal transmembrane region or other types of mutations, e.g., T-DNA insertion producing a "knock-down-type" or "loss-of-function-type" mutation, whereby the genes and the protein encoded by the gene is either a null allele or has reduced functionality (Table 2).

TABLE 1

CESA polypeptide mutations conferring beneficial saccharification properties.

| Gene | Mutation | Gene ID |
|------|----------|---------|
| CESA-3 | T9421 | At5g44030 |
| CESA-6 | R1064W | At5g64740 |
| CESA-3 | G998D | At5g44030 |
| CESA-1 | A903V | At4g32410 |

TABLE 2

CESA polypeptide mutations conferring no beneficial saccharification properties.

| Gene | Mutation | Gene ID |
|------|----------|---------|
| CESA-1 | A549V | At4g32410 |
| CESA-2 | T-DNA insertion | At4g39350 |
| CESA-6 | T-DNA insertion | At5g64740 |
| CESA-9 | T-DNA insertion | At2g21770 |
| CESA-10 | T-DNA insertion | At2g25540 |

Gene IDs as set forth in Tables 1 and 2 make reference to the *Arabidopsis* Information Resource (TAIR) database, which is readily available for access online. The sequences cross-referenced in the TAIR database are expressly incorporated by reference as are equivalent and related sequences present in the TAIR or other public databases. Also expressly incorporated herein by reference are all annotations present in the TAIR database associated with the sequences disclosed herein. Unless otherwise indicated or apparent the references to the TAIR database are references to the most recent version of the database as of the filing date of this Application.

Example I

Materials and Methods: Plant Material and Sample Collection.

Mutants used in this Example have either been previously published as or were isolated as homozygous T-DNA insertional alleles screened from the ABRC stock center, and include CESA-3 T942I ("ixr1-2"), CESA-6 R1064W ("ixr2-1"), CESA-1 A549V ("rsw1-2"), CESA-2 T-DNA insertion, CESA-6 T-DNA insertion, CESA-9 T-DNA insertion, CESA-10 T-DNA insertion, and other mutants. These plants (*Arabidopsis thaliana*) were grown at 22° C. under a 16 h light 8 h dark regime in crops of 50 plants and harvested as aerial plant biomass. Three independent growing cycles and analysis were performed for top candidates.

Materials and Methods: Micro-Scale Enzymatic Saccharification.

Celluclast 1.5 L (cellulase from *Trichoderma reesei*) and Novozyme 188 (cellobiase from *Aspergillus niger*) were purchased from Sigma-Aldrich. The enzyme cocktail was obtained by mixing equal volumes of the two enzymes that contained an enzymatic activity of 486 endoglucanase units (EGU) ml-1 for cellulase (45.6 FPU) and 134 CBU ml-1 for cellobiase. Enzymatic saccharification of lignocellulosic material was according to the laboratory analytical procedure of the National Renewable Energy Laboratory (LAP-009). Cellulose contents were measured spectrophotometrically (ThermoFischer Biomate3, Madison, Wis.) on homogeneous samples of 150 ground whole *Arabidopsis* plants and sugar release values are a percentage of this total (15, 16). Modification for the micro-scale experiment was made by using dry biomass samples equivalent to 0.02 g cellulose. In addition, the total reaction volume was reduced to 2 ml and a range of enzyme concentrations based on cellulase activity were used including 60 FPU, 30 FPU, 15 FPU and 7.5 FPU. The samples were incubated in an Innova 4300 incubator/shaker (New Brunswick Scientific) at 50° C. while shaking in a horizontal position at 100 RPM. The progress of the reaction was measured by taking representative 100 μl aliquots at 2, 4, 6, 12, 24, 72 and 168 hours. Enzyme blanks and Whatman #1 filter paper were digested alongside the samples.

Materials and Methods: X-Ray Scattering

Samples were prepared by oven-drying biomass at 60° C. for 36 hours. Alternative temperatures for the drying regime were used, such as 37° C. for 7 days or 80° C. for 12 hours followed by 110° C. for two hours, neither of which altered the RCI value measured in *Arabidopsis* tissue (similar to 13). Tissue was then homogenized using as Arthur H Thomas Co Scientific grinder (Philadelphia, Pa.) equipped with a 1 mm sieve. Biomass samples were then contained in a custom built sample holder of pressed boric acid. In brief, plant material was placed into a mold, containing a sleeve and hand pressed with a solid metal plug forming a disk shape. The sleeve and plug were removed and a boric acid (Fischer, Madison, Wis.) base was then formed by pouring the boric acid over the bottom and sides of the sample and applying 40,000 psi of pressure to the 40×40 mm mold using a Carver Autopellet Press (Wabash, Ind.). Samples were pressed to create an even horizontal surface. A Bruker-AXS Discover D8 Diffractometer (Bruker-AXS USA, Madison, Wis.) was used for wide angle X-ray diffraction with Cu Kα radiation generated at 30 mA and 40 kV. The experiments were carried out using Bragg-Brentano geometries (symmetrical reflection). Diffractograms were collected between 2° and 70° or 2° and 40° (for samples with little baseline drift), with 0.02° resolution and 2 s exposure time interval for each step. Sample rotation to redirect the x-ray beam diffraction site was achieved per replicate. *Arabidopsis* material was grown under both greenhouse and growth chamber for analysis. The data analysis was carried out using the calculation for relative crystallinity index (Weimer et al., 1995) of: $RCI = I_{002} - I_{am}/I_{002} \times 100$, where $I_{002}$ is the maximum peak height above baseline at approximately 22.5° and $I_{am}$ is the minimum peak height above the baseline at ~18° (Weimer et al., 1995). Peaks at the 22.5° and 18° were consistent with a control of synthetic crystalline cellulose (Avicel®)(FMC-Biopolymer, Philadelphia, Pa.) (Andersson et al., 2004). For assessment of experimental accuracy, the pressed samples were examined using reflective geometries at 22.5° 2-theta with the sample scanned rotationally (360°) and in an arc) (90° to obtain an intensity/spatial orientation plot of a sample for which the RCI had already been established. The range of reflective intensities was then used to estimate the accuracy of the RCI determination using a 95% cutoff across the plot range (13). Three experimental replicates for mutant and wild type biomass samples were performed. Diffractograms were collected in Diffrac-Plus-XRD Commander software (Bruker-AXS, Karlsruhe, Germany) and minimally processed (baseline identification, noise correction, 3D display and cropping of RCI signature region) using the EVA and TexEval (Bruker-AXS Karlsruhe, Germany) software.

Materials and Methods: Enzyme Kinetics.

The initial rate of sugar release using identical enzyme cocktail loadings (Celluclast 1.5 and Novozyme 188) as a function of substrate concentration was obtained by performing a similar micro-scale experiment as that conducted for the saccharification analysis. Dry biomass samples equivalent to sequentially increasing amounts of mutant and wild type plant derived cellulose were mixed with enzyme (7.5 FPU) and incubated for 2 hours. Similar to LAP-009 saccharification experiments and using the same enzyme buffer solution, the samples were incubated in an Innova 4300 incubator/shaker (New Brunswick Scientific) at 50° C. while shaking in a horizontal position at 100 RPM. The progress of the reaction was measured by taking individual aliquots at 2 hours and determining the glucose concentration using a YSI-glucose analyzer standardized for glucose determination using YSI buffer and membranes purchased from Yellow Springs Instruments (YSI, Yellow Springs, Ohio). Enzyme blanks and Whatman #1 filter paper were digested alongside the samples. The inability to exactly calculate catalytic ends in the complex mixture of cell wall biomass allowed only the calculation of a relative estimation, expressed as apparent kinetics values. Hence, classical Michaelis-Menten kinetics are not determined and the $K_m$ and $V_{max}$ values are apparent $K_m$ and $V_{max}$ relative estimates. These were generated and plotted in the statistical graphing program Graphpad Prism-4 (Graphpad, La Jolla, Calif.).

Materials and Methods: HPLC Analysis.

Fermentable sugars released by enzymatic hydrolysis were measured by high performance liquid chromatography. The enzymatic hydrolysates were injected into an eluent of 19 mM NaOH introduced at 1 ml·min$^{-1}$ using a Bio-LC HPLC (Dionex Corp, Palo Alto, Calif., USA) and separated through anion exchange using a Carbo-Pac PA1 with guard column (Dionex). Signal strength from a pulsed electrochemical cell monitoring eluting sugars in column effluent was integrated using PeakNet software. Sugars were identified and quantified by comparing their retention times and peak areas with that of known standards.

Materials and Methods: Cellulose Content Measurement.

Crude cell walls were prepared as published previously (Reiter et al., 1993). Briefly the samples for the measurement were homogenized using an Arthur H Thomas Co Scientific grinder (Philadelphia, Pa.) equipped with a 1 mm sieve. 25 mg plant material were incubated in 1 ml 70% ethanol overnight at 65° C., and washed twice with 1 ml 70% ethanol for 1 hour and once with 1 ml acetone for 5 min. After removing the washing solutions the samples were dried under vacuum. Cellulose content determination was done using the Updegraff method (Updegraff 1960) whereby 5 mg of the dry biomass extract were weighed out in triplicates from either wild type or mutant plants and boiled in acetic-nitric reagent (acetic acid:nitric acid: water 8:1:2) for 30 minutes to remove lignin and hemicellulose. The samples were allowed to cool down to RT and the reagent were carefully removed. The plant cell wall material was washed twice with 8 ml MQ-water and 4 ml acetone, and dried under vacuum. The cellulose samples were then hydrolyzed in 67% sulphuric acid for 1 hour. The glucose content of the samples was determined by the anthrone method (Scott and Melvin, 1953). 25 µl of the sulfuric acid hydrolyzed samples were mixed with 475 µl water and 1 ml 0.3% anthrone in concentrated sulphuric acid on ice. The samples were boiled for 5 minutes then placed immediately back on ice. The absorbance of the samples was measured using a Bio-Mate thermo scientific spectrophotometer (Thermo Fischer, Waltham, Mass.) set at OD 620 and compared to a standard curve obtained from known (10-50 mM) concentrations of glucose (the standard curve was set each time together with the reaction). The cellulose content was calculated by multiplying the measured glucose concentration of each sample by the total volume of the assay and then by the hydration correction factor of 0.9 (to correct for the water molecule added upon hydrolysis of the cellulose polymer).

Materials and Methods: Statistical Analysis.

Analysis of variance was conducted using the freeware statistical program R (Auckland, NZ) to test the null hypothesis of no statistical differences in RCI values between the transgenic plants and wild type. The null hypothesis was rejected at the 0.05 level. Nonlinear regression analysis was performed using the statistics program built into GraphPad Prism.

Results and Discussion.

Figure 5:
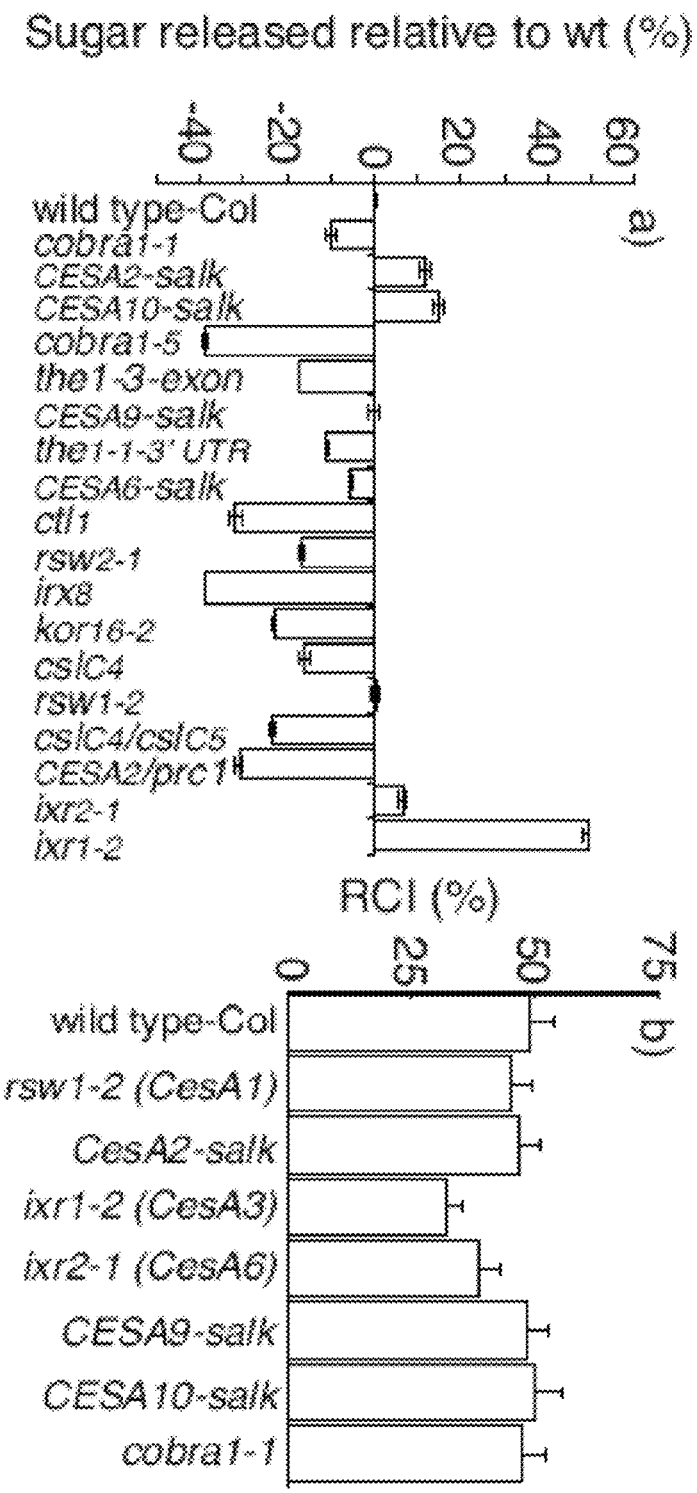
FIGS. 5A and 5B are bar graphs showing improved biochemical conversion of dry biomass into fermentable sugars in the cell wall mutants.

To establish whether genetic mutations in genes central to cell wall synthesis resulted in increased enzymatic saccharification, *Arabidopsis* plants containing homozygous T-DNA insertions or point mutations in different genes potentially involved in cellulose biosynthesis as well as plants with mutations conferring resistance to cell wall synthesis inhibitors were selected. Cellulose content was determined and each mutant analyzed for recalcitrance to saccharification after 24 h of enzymatic digestion using a commercial combination of cellulase cocktail from *Trichoderma reesei* (Sigma-Aldrich, St Louis, Mo.) (FIG. 5A). Four of the mutants analyzed, ixr1-2, ixr2-1, cesa2-salk and cesa10-salk yielded significantly more fermentable sugar than wild type (FIG. 5A). However, the ixr1-2 mutant, which contains a point mutation in CESA3 and is a compulsory subunit in the cellulose synthesizing machinery (9) displayed greater than 3-fold improvement in saccharification than the next closest candidate (CESA10). The ixr2-1 mutant contains a point mutation in the CESA6 (10) subunit and the CESA2 and CESA10 mutants, cesa2-salk and cesa10-salk, respectively, contain T-DNA insertions. These latter three plants were not selected as top candidates for study in these Examples because CESA2 and CESA6 are partially redundant and gene expression is limited to elongating tissue (11, 12), while knockout of CESA10 also displayed a minimal increase in cellulose conversion compared with ixr1-2.

Hence, by candidate list refinement using saccharification as the selection criteria we focused on the missense mutant ixr1-2 for further detailed analysis in these examples. It is noteworthy that several mutants displayed negative conversion potential relative to wild type biomass such as irx8 (FIG. 5A). In particular, it is noted that these mutants are knockouts. Thus, overexpressing these genes can potentially improve RCI and saccharification as well.

The possibly of creating "flawed" cellulose by genetic means has been considered highly challenging to plant scientists (2, 5). To approach this problem a second screen was performed on selected mutant plants identified in the saccharification screen using x-ray scattering analysis. This approach was used to generate a relative crystallinity index (RCI) (FIG. 5B) that correlates with changes in the orientation, size and/or density of the cellulose crystallites (13). Five out of the 7 plants tested displayed RCI values similar to that of wild type (48.9%±4.5). However, two mutants were identified as having lower RCI values than wild type and these were ixr1-2 (31.9±3.4%) and ixr2-1 (38.6±3.8%)(FIG. 5B).

Both of these mutants were identified in a forward chemical genetics screen as conferring resistance to the cellulose synthesis inhibitor isoxaben (14) and both mutant alleles displayed improved cellulose conversion efficiencies (FIG. 5A). Positional cloning revealed that both ixr1-2 and ixr2-1 have mutations in a CESA3 and CESA6 respectively and in both cases the location of the mutation is within the carboxyl terminus of each protein in or near one of the 8 transmembrane spanning domains (9, 10) (FIG. 2).

The similar mutations in different but related proteins confer isoxaben resistance, increased saccharification efficiency and reduced RCI value in both proteins. With respect to the latter two characteristics, and without wishing to be bound by any particular theory of operation, these mutations can possibly create structural changes in the proteins that alter their orientation within the CESA membrane complex, giving rise to irregular angles at which they produce and incorporate their glucan chain into the growing microfibril. This repositioning can possibly disrupt a certain percentage of hydrogen bonding within the microfibril causing an increase in amorphous zones along the fibril length which can contribute to a reduction in RCI in the biomass sample and an increase in accessibility to enzymatic hydrolysis. In addition, the partial redundancy between CESA6 and other CESA isoforms (see, FIG. 3) could help explain why the present data indicates that ixr2-1 displays similar RCI and enzymatic hydrolysis characteristics as ixr1-2, albeit not to the same extent.

Figure 6:
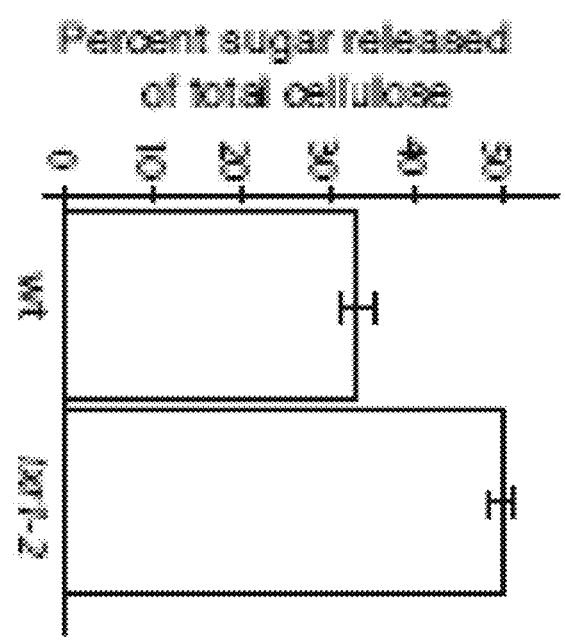
FIG. 6 is a bar graph plotting the fermentable sugars enzymatically released from wild type versus mutant as absolute values. Absolute values are the percent of total cellulose converted to fermentable in 24 hours using 60 FPU of enzyme (n=3)
Figure 7:
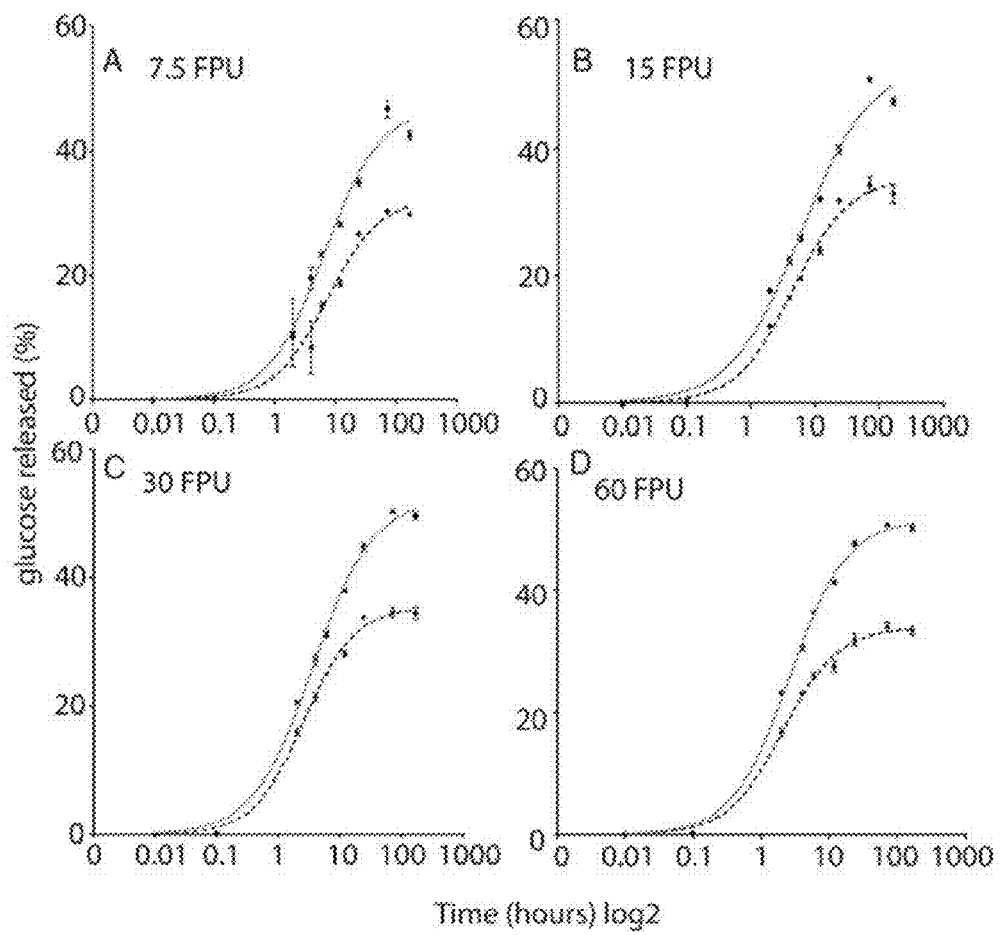
FIGS. 7A-7D are line graphs showing saccharification efficiency reported as % of total glucose released at 2, 4, 6, 12, 24, 48, and 168 hours using (A) 7.5, (B) 15, (C) 30 and (D) 60 FPU of enzyme from wild type (dashed line) and ixr1-2 (solid line) (error bars n=4).

Data plotted as percent of absolute cellulosic biomass converted to fermentable sugar showed that where wild type plants released less than a third of their total cellulose upon enzymatic hydrolysis (168 h) the ixr1-2 mutant released greater than 50% of its total cellulose as fermentable sugar (FIG. 6). A more detailed saccharification experiment was conducted on the ixr1-2 mutant by measuring 8 time points from zero to 168 hours and using four different enzyme concentrations ranging from 7.5 filter paper units (FPU) to 60 FPU. The results indicated three areas where ixr1-2 showed marked improvement over wild type: fermentable sugar released at the 168 hour time point was 151% that of wild type; at each time point a larger percent of fermentable sugar was released in ixr1-2 compared with wild type (FIGS. 7A-7D); more sugar released using eight fold less enzyme (FIG. 7A compared with FIG. 7D). Increasing energy costs on top of the already costly chemical and heat pretreatment to improve the saccharification efficiency of cellulosic biomass (2) suggests that genetic improvement of the cellulosic substrate to both reduce enzyme costs as well as improve fermentable sugar yields can enhance the viability of cellulose as an alternative to starch based ethanol (3).

Figure 8:
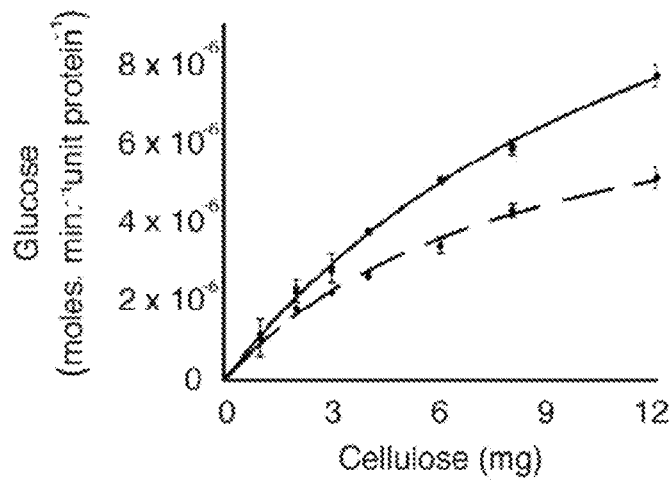
FIG. 8 is a line graph showing initial rate of sugar release from biomass by the enzyme mixture as a function of cellulose concentration. Wild type biomass closed circles and dashed line and ixr1-2 closed squares and solid line (error bars n=3).
Figure 9:
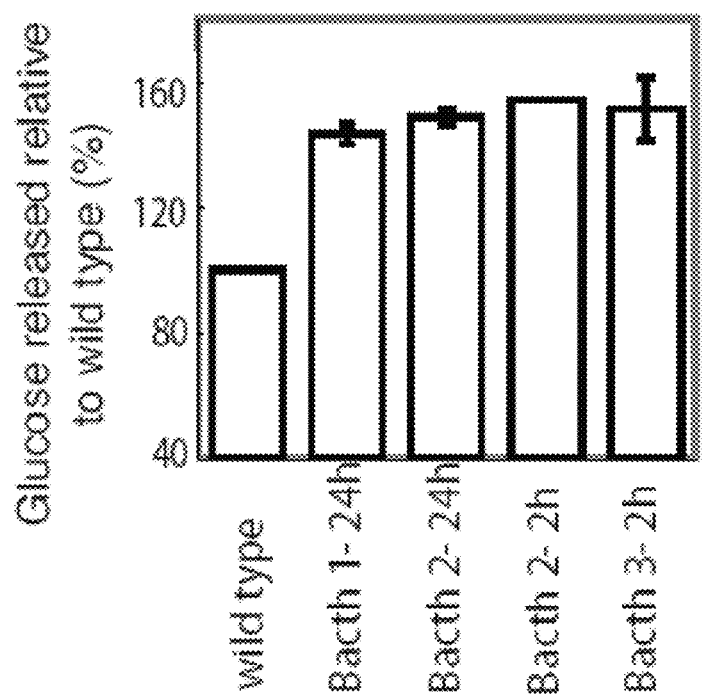
FIG. 9 is a bar graph showing a consistent 50% improvement in the ixr1-2 mutant over bioconversion of wild type lignocellulosic biomass in batch and time comparison studies.

In order to explore the nature of the improved biochemical catalysis measured using the complex of multiple cellulase enzymes from *T. reesei* and the complexity of the biomass substrate used during these experiments we calculated an apparent $_{app}V_{max}$ and $_{app}K_m$: wild type displayed $_{app}V_{max}$ and $_{app}K_m$ of 3.792 mM/2 h and 10.26 mg, ixr1-2 of 7.144 mM/2 h and 16.55 mg. A relative estimation of an apparent specificity-like constant ($_{app}V_{max}/K_m$) provided the calculation of relative affinity of the enzyme complex to the cellulose substrate compared between wild type ($_{app}V_{max}/K_m$=0.368) and ixr1-2 (0.432) (FIG. 8). Kinetic data showed that the mutant plant produced a cellulose substrate that was more readily broken down by the digestion enzyme cocktail, as indicated by the higher $_{app}V_{max}$ value, and suggested a greater relative catalytic efficiency (affinity) for the enzyme complex towards the mutant plant cellulose as indicated by the higher $_{app}V_{max}/K_m$ ratio (FIG. 8). Batch and time comparisons showed a consistent 50% improvement in the ixr1-2 mutant over bioconversion of wild type lignocellulosic biomass (FIG. 9).

In conclusion, genetic modification of the primary cell wall CESA genes by missense mutations demonstrates the capacity to alter the efficiency at which the cellulosic biomass is converted to fermentable sugars. The ubiquitous nature of CESA3 orthologs in the primary cell wall of higher plants (6) (FIG. 3) indicates that the outcome of these examples can have high value in the development of feedstock grasses for both the bio fuels and forage industry. Further, since the ixr1-2 mutation occurs in the compulsory primary cell wall cellulose synthase subunit number 3, efforts to generate the same amino acid change in the C terminal transmembrane region of the secondary cell wall CESA subunits (CESA4, 7 and 8) can be similarly effective in lowering RCI and increasing saccharification efficiency. Hence, the present examples support a rational strategy to similarly improve the efficiency of biomass conversion from any number of crops, including tree crops such as Populus, particularly due to the conserved sequences across species in the C terminal transmembrane spanning regions of the CESA proteins (FIGS. 2 and 3).

Example II

Figure 11:
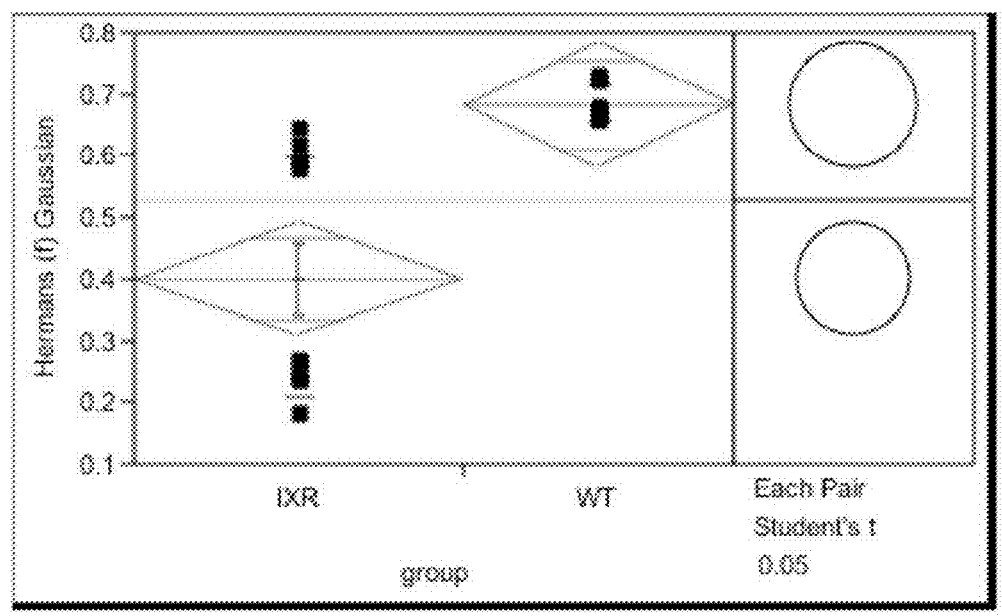
FIG. 11 includes the results of wide angle synchrotron analysis used to study structural changes in cellulose derived from a ixr1-2 plant, as compared to cellulose derived from a control plant.

Wide angle synchrotron (Cornell University) analysis was used to further elucidate the structural changes in cellulose derived from the ixr1-2 plant versus wild type (FIG. 11). A significantly difference fiber orientation between WT and IXR1-2 was found. Mutant fibers are less orientated in relation to the fiber axis. There is no significant difference in crystallite dimension between WT and IXR1-2, but there was a significant decrease in the crystallinity of the cellulose polymorphs. This data further exemplifies the findings described herein using higher resolution x-ray analysis. General information about using synchrotron analysis to study cellulose can be found in Wada M, Okano T, Sugiyama J (1997) "Synchrotron-radiated X-ray and neutron diffraction study of native cellulose," *Cellulose* 4:221-232, which is incorporated herein by this reference.

Example III

Studies with a plant (*Arabidopsis thaliana*) expressing a CESA-1 with a A903V mutation ("qxr" or "ags") have shown significant reorganization of the mutant cell wall. Feedback between the gene mutation and cell wall structure was determined by FTIR analysis of the polysaccharide fingerprint region. The following conclusions were ascertained; firstly, the qxr mutant has aberrant root hair formation, which can be observed using light microscopy and have been described for cell wall gene deletion alleles. The highly elongated cell shape of root hairs has been used as model to define molecular players in cell elongation and a plausible explanation for the altered root hair phenotype is consistent with a defect in cell wall structure. Given this phenotype, the present inventors explored whether rapidly elongating tissue such as roots or hypocotyls of qxrseedlings grown in the dark were different and found that no measurable changes. Next, the inventors explored whether treating qxr mutants with the cellulose inhibitor isoxaben at minute doses induced a synergistic effect. The results showed that qxr grown on plates containing 2 nM isoxaben alongside wild type plants displayed dramatically swollen organs, whereas the wild type did not.

It was determined that the qxr mutant included a single base mutation conferred an amino acid 903 from an alanine to a valine in the C-terminal transmembrane region of CESA-1. Analysis of altered cellulose structure was performed on mutant plants using X-ray scattering analysis, as described herein, to generate a relative crystallinity index (RCI) that established possible changes in the orientation, size or density of the cellulose crystallites. X-ray diffraction patterns showed consistent signature peak distribution with previous published reports (Weimer et al., 1995) and these were overlayed with synthetic crystalline cellulose (Avicel) to determine the relative crystallinity index for synthetic crystalline cellulose (Weimer et al., 1995, Harris and DeBolt, 2008). The experimental accuracy was approximated by determining the noise in the diffractogram using a Phi and Chi scan (360° rotational by 90° in an arc in the x-ray diffractometer) of the sample, creating an intensity/spatial orientation plot at 22.5° 2-theta and was determined to contribute approximately 10% error, which was added variability between replicates.

RCI provided a screening tool for sample crystallinity of which the crystalline polymer within the complex mixture of polysaccharides is cellulose. Examination of mutant alleles compared with wild type parental lines were performed in triplicate. The RCI of wild type parental lines was measured to be 48.9%±4.5. and for the aegeus mutant 38.6±4.2%. These data are consistent with data for the plant including the CESA-3 T942I mutation, providing further evidence that a mutation in the c-terminal transmembrane region of a CESA polypeptide confers beneficial saccharification properties.

Example IV

CESA-3 G998D ("ixr1-1"). The ixr1-1 mutation, like ixr1-2, results in high level of resistance to the herbicide N-(3-[1-ethyl-1-methylpropyl]-5-isoxazo lyl)-2,6,dimethoxybenzamide (isoxaben); resistance of ixr1-1 is greater than that of ixr1-2 with approximately 300 times the drug tolerance of wild type for homozygotes. Scheible, et al. (2001). The ixr1-1 mutation is a single nucleotide substitution in the last exon (G11204A) leading to a Gly998Asp amino acid change. The location of the mutation is therefore also in the C-terminal transmembane region of the CESA3 protein. Analysis of altered cellulose structure was performed on mutant plants using X-ray scattering analysis, as described herein, to generate a relative crystallinity index (RCI) that established possible changes in the orientation, size or density of the cellulose crystallites. X-ray diffraction patterns showed consistent signature peak distribution with previous published reports (Weimer et al., 1995) and these were overlayed with synthetic crystalline cellulose (Avicel) to determine the relative crystallinity index for synthetic crystalline cellulose (Weimer et al., 1995, Harris and DeBolt, 2008). These data showed that ixr1-1 has an RCI value of 34% relative to 50% for wild type. The percent of absolute cellulosic biomass converted to fermentable sugar was calculated and showed that where wild type plants released less than a third of their total cellulose upon enzymatic hydrolysis (168 h) the ixr1-1 mutant also released greater than 50% of its total cellulose as fermentable sugar, which was highly consistent with the data gathered for ixr1-2.

Example V

Studies will be performed to introduce CESA polypeptide mutations into *Populus tremuloides*. The homology of CESA genes across taxa is high. Since the Poplar genome is complete and annotated the identification of the CESA3 homolog has already been achieved. A polynucleotide encoding CESA-3 T942I will be introduced into poplar using the KTRDC expression vectors for high efficiency plant transformation. As described in the examples above, this technology has been developed in *Arabidopsis*. In order to facilitate the development of new feedstocks for bioenergy agriculture, this technology will be incorporated into non-model plants. Many scientists are looking at non-food sources for biomass, including grasses and woody crops (20). This is because using food crops for bioenergy will threaten national security and cutting forest for bioenergy will accelerate green house gas emission (21). Lignocellulosic biomass for bioenergy agriculture presents a sustainable bioenergy solution and this project is targeted as improving this process.

*P. tremuloides* is the most wide-spread tree species in North America, and its rapid growth generates the most abundant wood-based biomass out of any other plant species. The poplar tree genome database is complete, and efficient transformation have been developed that are suitable for high-throughput format transformations using *Agrobacterium tumefaciens* to produce transformed trees. The most rapid method uses *Agrobacterium* inoculated aspen seedling hypocotyls followed by direct thidiazuron (TDZ)-mediated shoot regeneration on selective media. KTRDC transformation facility will be provided all relevant protocols that can be adapted to their patented technology. Transformation will be verified screening for isoxaben resistance conferred by the ixr1-2 mutation in addition to the selectable marker that will be introduced in the binary vector.

The following description is provided with reference to FIG. 10, which is a schematic map of the plant expression constructs (pKM24-CESA3-1, pKM24-CESA3-2, pKM24-CESA3-3) with the chimeric CESA3 gene (GenBank accession no. NM120599). The modified full-length transcript promoter (M24) of the Mirabilis mosaic virus (Maiti et al., 2002; Dey and Maiti, 1999; Dey and Maiti 1999) directs the coding sequences of respective CESA3 and fused GFP-CESA3 genes. A translational enhancer sequence (5'amv) 35-nt long 5'-untranslated region of A1MV RNA 4 was fused with the gene. An apoplast targeting sequence (aTP) of *Arabidopsis* 2S2 protein gene was fused with the coding sequence of CESA3 and GFP-CESA3 in construct pKM24CESA3-2 and PKM24-CESA3-3, respectively. LT, left T-DNA border; RT, right T-DNA border; KanR, neomycin phosphotransferase II marker gene directed by nopaline synthase promoter (NosP), the 3'-terminator sequences (Terminators) of ribulose bisphosphate carboxylase small subunits (3'RbcS) and nopaline synthase (3' Nos) genes are also shown. The EcoRI, XhoI, SstI, NcoI and ClaI restriction sites used to assemble these expression vectors are shown.

Regenerated mutant plants will be grown in the presence of isoxaben to select those carrying a stable mutant copy of the Ptixr1-2 gene. Exogenous application of ixoxaben by aerial spraying will inoculate plants and confirm that the mutated gene is present in the plant, since previous studies have shown isoxaben to be lethal at 5 nM dose.

In order to explore the structural changes in the cellulose microfibril conferred by the Pt-ixr1-2 mutation a brief window of time will been booked for the use of the Cornell High Energy Synchrotron Source (CHESS). There exist established protocols to examine cellulose structure by synchrotron analysis based on the methods of Nishimaya et al. (19) that provide higher resolution than wide-angle x-ray scattering approaches we have used (13, 22). This method has been used to analyze the At-ixr1-2 mutant and it is evident that hydrogen bonding is lower in the cellulose crystallites. With the increased energy and resolution provided by the synchrotron the exact changes in cellulose structure in the Pt-ixr1-2 mutant will be able to be established, whether it be density, length or absolute crystallinity. Contemplated analyses include the following. Analysis of lignification by phloroglucinol staining Compensatory response is also of interest, for instance, in some plants, removal of cellulose results in increases amorphous glucose (callose) and other cell wall neutral sugars. Many of these are easily converted to bio fuel, pulp and paper and forage and will therefore be of great interest. The digestibility of the ground woody biomass into biofuel will be determined by the mciro-scale saccharification process established by the present inventors (22). The outcome will be a quantification of the improved digestibility traits in the Pt-ixr1-2 mutant relative to wild type.

Refine molecular phenotype in the Pt-irxl-2 mutant by performing quantitative live cell imaging of GFP labelled CESA complex velocity, activation time differ between mutant and wild type plants. N-terminal GFP fusion constructs are therefore selected in FIG. 10 for generating chimeric proteins. The ability to visualize changes in the localization and activity of CESA in real time will be valuable for testing the mutant Pt-ixr1-2. Tagged CESA protein has been observed to arrive at the PM where it activates and moves while tracking cortical microtubules. Measurable observations are velocity (constant or variable rate of membrane complex movement, variation among individual complexes), orientation (angle of movement), CESA complex density per linear unit (mm), dynamics of internal CESA compartments and time spent at the membrane prior to activation.

Increasing the cellulose content and digestibility are important for more efficient bio fuel production. However, these have a tendency to reduce the stem strength that affects lodging and other agronomic factors (23). Numerous studies have evaluated the mechanical parameters that affect stem strength (24, 25) and some have looked at the power required to grind biomass (26). A question that has not been answered is how incremental changes in the cellulose characteristics affect plant strength. Moreover, how do other components of the cell wall respond to modifications in cellulose. These will ultimately lead to a thorough phenotypic analysis of the low crystalline cellulose poplar entries for lignin, cellulose content and hemicellulose content relative to wild type plants.

Several basic mechanical properties such as ultimate tensile strength, parallel-to-fiber crushing strength, perpendicular-to-fiber crushing strength, and shearing strength must be quantified in order to compare various genotypes. The aforementioned parameters for Poplar will be acquired using a table top computer-controlled electro-mechanical universal testing machine and employing ASTM standard D143-94 (2007) *Standard Test Methods for Small Clear Specimens of Timber* as a guideline. ASTM D143 will be a guideline solely based on the fact that the compressed timetable of this investigation will not allow the harvest of specimens of the proper size. Clearly, *Brachypodium* is a grass and as such will require the use of a specifically tailored testing regimen. This regimen will utilize the equipment and procedure as described by (23)

because they have devised solutions to many grass-specific concerns pertaining to strength measurement.

Sequences described herein are described with reference to GENBANK® accession numbers and SWISSPROT identification numbers. (GENBANK® accession numbers: CESA1-BX827280, CESA2, NM_120095, CESA3-AF027174, CESA4-BX833432, CESA5-NM 121024, CESA6-H36985, CESA7-NM 121784, CESA8-NM 111994, CESA9-NM 127746, CESA10-NM 128111; SWISSPROT identification numbers: CESA1-048946, CESA2-048947, CESA3-Q941L0, CESA4-Q84JA6, CESA5-Q8L778, CESA6-Q94JQ6, CESA7-Q9SWW6, CESA8-Q8LPK5, CESA9-Q9SJ22, CESA10-Q9SKJ5). The sequences cross-referenced in the GENBANK® and SWISSPROT databases are expressly incorporated by reference as are equivalent and related sequences present in GENBANK®, SWISSPROT, or other public databases. Also expressly incorporated herein by reference are all annotations present in the GENBANK® and SWISSPROT databases associated with the sequences disclosed herein. Unless otherwise indicated or apparent the references to the GENBANK® database and the SWISSPROT database are references to the most recent version of the database as of the filing date of this Application.

While the terms defined herein are believed to be well understood by one of ordinary skill in the art, the definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

Throughout this document, various references are mentioned. All such references are incorporated herein by reference, including the references set forth in the following list:

REFERENCES

1. Farquhar G D, von Caemmerer S, Berry J A (2001) Models of photosynthesis. Plant Physiol 125: 42-45.
2. Schmer M R, Vogel K P, Mitchell R B, Perrin R K (2008) Net Energy of Cellulosic Ethanol from Switchgrass. Proc Natl Acad Sci USA 105: 464-469.
3. Stricklen M B (2008) Plant genetic engineering for bio fuel production: towards affordable cellulosic ethanol Nature Rev Gen 9: 433-443.
4. Chen F, Dixon R A (2007) Lignin modification improves fermentable sugar yields for bio fuel production Nature Biotechnol 25: 759-761.
5. Gomez L D, Steele-King C G, McQueen-Mason SJ (2008) Sustainable liquid biofuels from biomass: the writing's on the walls New Phytol 178: 473-485.
6. Mutwil M, DeBolt S, Persson S (2008) Cellulose synthase; a complex complex. Curr Opin Plant Biol 11: 252-257.
7. Somerville C (2006) Cellulose synthesis in higher plants. Annu Rev Cell Dev Biol 22: 53-78
8. Nishiyama Y, Chanzy H, Wada M, Sugiyama t J, Mazeau K, et al. (2002) Synchrotron X-ray and neutron fiber diffraction. Adv X-ray Anal 45: 385-390.
9. Scheible W R, Eshed R, Richmond T, Delmer D, Somerville C R (2001) Modifications of cellulose synthase confer resistance to isoxaben and thiazolidinone herbicides in Arabidopsis Ixr1 mutants. Proc Natl Acad Sci USA 98: 10079-10084.
10. Desprez T, Vernhettes S, Fagard M, Refrégier G, Desnos T, Aletti E, Py N, Pelletier S, Hofte H (2002) Resistance against herbicide isoxaben and cellulose deficiency caused by distinct mutations in same cellulose synthase isoform CESA6. Plant Physiol 128: 482-490.
11. Desprez T, Juraniec M, Crowell E F, Jouy H, Pochylova Z, Parcy F, Hofte H, Gonneau M, Vernhettes S. (2007) Organization of cellulose synthase complexes involved in primary cell wall synthesis in Arabidopsis thaliana. Proc Natl Acad Sci USA 104: 15572-15577.
12. Persson S, Paredez A, Carroll A, Palsdottir H, Doblin M, Poindexter P, Khitrov N, Auer M, Somerville CR (2007) Genetic evidence for three unique components in primary cell-wall cellulose synthase complexes in Arabidopsis. Proc Natl Acad Sci USA 104: 15566-15571
13. Harris D, DeBolt S (2008) Relative Crystallinity in Plant Biomass: Studies on Assembly, Adaptation and Acclimation PLoS ONE 3(8): e2897. doi:10.1371/journal.pone.0002897
14. Heim D R, Skomp J R, Tschabold E E, Larrinua I M (1990) Isoxaben inhibits the synthesis of acid insoluble cell-wall materials in Arabidopsis thaliana. Plant Physiol 93: 695-700.
15. Updegraff D M (1969) Semimicro determination of cellulose in biological materials. Analyt Biochem 32: 420-424.
16. Reiter W-D, Chapple C C S, Somerville C R (1993) Altered growth and cell walls in a fucose-deficient mutant of Arabidopsis. Science 261: 1032-1035.
17. Himmel M E, Ding S Y, Johnson D K, Adney W S, Nimlos M R, Brady J W, Foust T D (2007) Biomass recalcitrance: Engineering plants and enzymes for biofuels production. Science 315: 804-807.
18. Andersson S, Wikberg H, Pesonen E, Maunu S L, Serimaa R (2004) Trees-Struct Funct 18: 346-353.
19. Nishimaya Y, Langan P, Chanzy H (2002) J. Am. Chem. Soc., 124 (31), 9074-9082.
20. Searchinger T, Heimlich R, Houghton R A, Dong F, Elobeid A, Fabiosa J, Tokgoz S, Hayes D, & Yu T-H (2008) Science 319, 1238-1240.
21. Hill J P S, Nelson E, Tilman D, Huo H, Ludwig L, Neumann J, Zheng H, Bonta D. (2009) Proc Natl Acad Sci USA 10.1073/pnas.0812835106.
22. Harris, D., Stork, J., DeBolt, S (2009) GCB Bioenergy 1, 51-61.

23. Mathur J & Koncz C S- (1998), eds. Martinez-Zapater J & Salinas J (Suite 808, 999 Riverview Drive, Totowa, N.J. 07512, USA: Humana Press Inc., 1998), pp. 35-42.
24. Besseau S, Hoffmann L, Geoffroy P, Lapierre C, Pollet B, & Legrand M (2007) *Plant Cell* 19, 148-162.
25. Thompson, D. L. (1963) *Crop Sci.* 3, 323-329.
26. Evans, L. S., Kahn-Jetter, Z., Marks, C., Harmoney, K. R. (2007) *Journal of the Torrey Botanical Society* 134,458-467.

---

CESA3 polynucleotide sequence (GenBank Accession No. NM_120599) SEQ ID NO: 1

ATGGAATCCGAAGGAGAAACCGCGGGAAAGCCGATGAAGAACATTGTTCCG
CAGACTTGCCAGATCTGTAGTGACAATGTTGGCAAGACTGTTGATGGAGAT
CGTTTTGTGGCTTGTGATATTTGTTCATTCCCAGTTTGTCGGCCTTGCTAC
GAGTATGAGAGGAAAGATGGGAATCAATCTTGTCCTCAGTGCAAAACCAGA
TACAAGAGGCTCAAAGGTAGTCCTGCTATTCCTGGTGATAAAGACGAGGAT
GGCTTAGCTGATGAAGGTACTGTTGAGTTCAACTACCCTCAGAAGGAGAAA
ATTTCAGAGCGGATGCTTGGTTGGCATCTTACTCGTGGGAAGGGAGAGGAA
ATGGGGGAACCCCAGTATGATAAGAGGTCTCTCACAATCATCTTCCTCGT
CTCACGAGCAGACAAGATACTTCAGGAGAGTTTTCTGCTGCCTCACCTGAA
CGCCTCTCTGTATCTTCTACTATCGCTGGGGGAAAGCGCCTTCCCTATTCA
TCAGATGTCAATCAATCACCAAATAGAAGGATTGTGGATCCTGTTGGACTC
GGGAATGTAGCTTGGAAGGAGAGAGTTGATGGCTGGAAAATGAAGCAAGAG
AAGAATACTGGTCCTGTCAGCACGCAGGCTGCTTCTGAAAGAGGTGGAGTA
GATATTGATGCCAGCACAGATATCCTAGCAGATGAGGCTCTGCTGAATGAC
GAAGCGAGGCAGCCTCTGTCAAGGAAAGTTTCAATTCCTTCATCACGGATC
AATCCTTACAGAATGGTTATTATGCTGCGGCTTGTTATCCTTTGTCTCTTC
TTGCATTACCGTATAACAAACCCAGTGCCAAATGCCTTTGCTCTATGGCTG
GTCTCTGTGATATGTGAGATCTGGTTTGCCTTATCCTGGATTTTGGATCAG
TTTCCCAAGTGGTTTCCTGTGAACCGTGAAACCTACCTCGACAGGCTTGCT
TTAAGATATGATCGTGAAGGTGAGCCATCACAGTTAGCTGCTGTTGACATT
TTCGTGAGTACTGTTGACCCCTTGAAGGAGCCACCCCTTGTGACAGCCAAC
ACAGTGCTCTCTATTCTGGCTGTTGACTACCCAGTTGACAAGGTGTCCTGT
TATGTTTCTGATGATGGTGCTGCTATGTTATCATTTGAATCACTTGCAGAA
ACATCAGAGTTTGCTCGTAAATGGGTACCATTTTGCAAGAAATATAGCATA
GAGCCTCGTGCACCAGAATGGTACTTTGCTGCGAAAATAGATTACTTGAAG
GATAAAGTTCAGACATCATTTGTCAAAGATCGTAGAGCTATGAAGAGGGAA
TATGAGGAATTTAAAATCCGAATCAATGCACTTGTTTCCAAAGCCCTAAAA
TGTCCTGAAGAAGGGTGGGTTATGCAAGATGGCACACCGTGGCCTGGAAAT
AATACAAGGGACCATCCAGGAATGATCCAGGTCTTCTTAGGGCAAATGGT
GGACTTGATGCAGAGGGCAATGAGCTCCCGCGTTTGGTATATGTTTCTGA
GAAAAGCGACCAGGATTCCAGCACCACAAAAAGGCTGGTGCTATGAATGCA
CTGGTGAGAGTTTCAGCAGTTCTTACCAATGGACCTTTCATCTTGAATCTT
GATTGTGATCATTACATAAATAACAGCAAAGCCTTAAGAGAAGCAATGTGC

---

CESA3 polynucleotide sequence (GenBank Accession No. NM_120599) SEQ ID NO: 1

TTCCTGATGGACCCAAACCTCGGGAAGCAAGTTTGTTATGTTCAGTTCCCA
CAAAGATTTGATGGTATCGATAAGAACGATAGATATGCTAATCGTAATACC
GTGTTCTTTGATATTAACTTGAGAGGTTTAGATGGGATTCAAGGACCTGTA
TATGTCGGAACTGGATGTGTTTTCAACAGAACAGCATTATACGGTTATGAA
CCTCCAATAAAAGTAAAACACAAGAAGCCAAGTCTTTTATCTAAGCTCTGT
GGTGGATCAAGAAAGAAGAATTCCAAAGCTAAGAAAGAGTCGGACAAAAAG
AAATCAGGCAGGCATACTGACTCAACTGTTCCTGTATTCAACCTCGATGAC
ATAGAAGAGGGAGTTGAAGGTGCTGGTTTTGATGATGAAAAGGCGCTCTTA
ATGTCGCAAATGAGCCTGGAGAAGCGATTTGGACAGTCTGCTGTTTTTGTT
GCTTCTACCCTAATGGAAAATGGTGGTGTTCCTCCTTCAGCAACTCCAGAA
AACCTTCTCAAAGAGGCTATCCATGTCATTAGTTGTGGTTATGAGGATAAG
TCAGATTGGGGAATGGAGATTGGATGGATCTATGGTTCTGTGACAGAAGAT
ATTCTGACTGGGTTCAAAATGCATGCCCGTGGATGGCGATCCATTTACTGC
ATGCCTAAGCTTCCAGCTTTCAAGGGTTCTGCTCCTATCAATCTTTCAGAT
CGTCTGAACCAAGTGCTGAGGTGGGCTTTAGGTTCAGTTGAGATTCTCTTC
AGTCGGCATTGTCCTATATGGTATGGTTACAATGGGAGGCTAAAATTTCTT
GAGAGGTTTGCGTATGTGAACACCACCATCTACCCTATCACCTCCATTCCT
CTTCTCATGTATTGTACATTGCCAGCCGTTTGTCTCTTCACCAACCAGTTT
ATTATTCCTCAGATTAGTAACATTGCAAGTATATGGTTTCTGTCTCTCTTT
CTCTCCATTTTCGCCACGGGTATACTAGAAATGAGGTGGAGTGGCGTAGGC
ATAGACGAATGGTGGAGAAACGAGCAGTTTTGGGTCATTGGTGGAGTATCC
GCTCATTTATTCGCTGTGTTTCAAGGTATCCTCAAAGTCCTTGCCGGTATT
GACACAAACTTCACAGTTACCTCAAAAGCTTCAGATGAAGACGGAGACTTT
GCTGAGCTCTACTTGTTCAAATGGACAACACTTCTGATTCCGCCAACGACG
CTGCTCATTGTAAACTTAGTGGGAGTTGTTGCAGGAGTCTCTTATGCTATC
AACAGTGGATACCAATCATGGGGACCACTCTTTGGTAAGTTGTTCTTTGCC
TTCTGGGTGATTGTTCACTTGTACCCTTTCCTCAAGGGTTTGATGGGTCGA
CAGAACCGGACTCCTACCATTGTTGTGGTCTGGTCTGTTCTCTTGGCTTCT
ATCTTCTCGTTGTTGTGGGTTAGGATTGATCCCTTCACTAGCCGAGTCACT
GGCCCGGACATTCTGGAATGTGGAATCAACTGTTGAGAAGCGAGCAAATAT
TTACCTGTTTTGAGGG

---

CESA3 polypeptide sequence (GenBank Accession No. NP_196136) SEQ ID NO: 2

MESEGETAGKPMKNIVPQTCQICSDNVGKTVDGDRFVACDICSFPVCRPCY
EYERKDGNQSCPQCKTRYKRLKGSPAIPGDKDEDGLADEGTVEFNYPQKEK
ISERMLGWHLTRGKGEEMGEPQYDKEVSHNHLPRLTSRQDTSGEFSAASPE
RLSVSSTIAGGKRLPYSSDVNQSPNRRIVDPVGLGNVAWKERVDGWKMKQE

| CESA3 polypeptide sequence (GenBank Accession No. NP_196136) SEQ ID NO: 2 |
|---|
| KNTGPVSTQAASERGGVDIDASTDILADEALLNDEARQPLSRKVSIPSSRI |
| NPYRMVIMLRLVILCLFLHYRITNPVPNAFALWLVSVICEIWFALSWILDQ |
| FPKWFPVNRETYLDRLALRYDREGEPSQLAAVDIFVSTVDPLKEPPLVTAN |
| TVLSILAVDYPVDKVSCYVSDDGAAMLSFESLAETSEFARKWVPFCKKYSI |
| EPRAPEWYFAAKIDYLKDKVQTSFVKDRRAMKREYEEFKIRINALVSKALK |
| CPEEGWVMQDGTPWPGNNTRDHPGMIQVFLGQNGGLDAEGNELPRLVYVSR |
| EKRPGFQHHKKAGAMNALVRVSAVLTNGPFILNLDCDHYINNSKALREAMC |
| FLMDPNLGKQVCYVQFPQRFDGIDKNDRYANRNTVFFDINLRGLDGIQGPV |
| YVGTGCVFNRTALYGYEPPIKVKHKKPSLLSKLCGGSRKKNSKAKKESDKK |
| KSGRHTDSTVPVFNLDDIEEGVEGAGFDDEKALLMSQMSLEKRFGQSAVFV |
| ASTLMENGGVPPSATPENLLKEAIHVISCGYEDKSDWGMEIGWIYGSVTED |
| ILTGFKMHARGWRSIYCMPKLPAFKGSAPINLSDRLNQVLRWALGSVEILF |
| SRHCPIWYGYNGRLKFLERFAYVNTTIYPITSIPLLMYCTLPAVCLFTNQF |
| IIPQISNIASIWFLSLFLSIFATGILEMRWSGVGIDEWWRNEQFWVIGGVS |
| AHLFAVFQGILKVLAGIDTNFTVTSKASDEDGDFAELYLFKWTTLLIPPTT |
| LLIVNLVGVVAGVSYAINSGYQSWGPLFGKLFFAFWVIVHLYPFLKGLMGR |
| QNRTPTIVVVWSVLLASIFSLLWVRIDPFTSRVTGPDILECGINC |

| CESA3 polypeptide sequence with T942I mutation SEQ ID NO: 3 |
|---|
| MESEGETAGKPMKNIVPQTCQICSDNVGKTVDGDRFVACDICSFPVCRPCY |

| CESA3 polypeptide sequence with T942I mutation SEQ ID NO: 3 |
|---|
| EYERKDGNQSCPQCKTRYKRLKGSPAIPGDKDEDGLADEGTVEFNYPQKEK |
| ISERMLGWHLTRGKGEEMGEPQYDKEVSHNHLPRLTSRQDTSGEFSAASPE |
| RLSVSSTIAGGKRLPYSSDVNQSPNRRIVDPVGLGNVAWKERVDGWKMKQE |
| KNTGPVSTQAASERGGVDIDASTDILADEALLNDEARQPLSRKVSIPSSRI |
| NPYRMVIMLRLVILCLFLHYRITNPVPNAFALWLVSVICEIWFALSWILDQ |
| FPKWFPVNRETYLDRLALRYDREGEPSQLAAVDIFVSTVDPLKEPPLVTAN |
| TVLSILAVDYPVDKVSCYVSDDGAAMLSFESLAETSEFARKWVPFCKKYSI |
| EPRAPEWYFAAKIDYLKDKVQTSFVKDRRAMKREYEEFKIRINALVSKALK |
| CPEEGWVMQDGTPWPGNNTRDHPGMIQVFLGQNGGLDAEGNELPRLVYVSR |
| EKRPGFQHHKKAGAMNALVRVSAVLTNGPFILNLDCDHYINNSKALREAMC |
| FLMDPNLGKQVCYVQFPQRFDGIDKNDRYANRNTVFFDINLRGLDGIQGPV |
| YVGTGCVFNRTALYGYEPPIKVKHKKPSLLSKLCGGSRKKNSKAKKESDKK |
| KSGRHTDSTVPVFNLDDIEEGVEGAGFDDEKALLMSQMSLEKRFGQSAVFV |
| ASTLMENGGVPPSATPENLLKEAIHVISCGYEDKSDWGMEIGWIYGSVTED |
| ILTGFKMHARGWRSIYCMPKLPAFKGSAPINLSDRLNQVLRWALGSVEILF |
| SRHCPIWYGYNGRLKFLERFAYVNTTIYPITSIPLLMYCTLPAVCLFTNQF |
| IIPQISNIASIWFLSLFLSIFATGILEMRWSGVGIDEWWRNEQFWVIGGVS |
| AHLFAVFQGILKVLAGIDTNFTVISKASDEDGDFAELYLFKWTTLLIPPTT |
| LLIVNLVGVVAGVSYAINSGYQSWGPLFGKLFFAFWVIVHLYPFLKGLMGR |
| QNRTPTIVVVWSVLLASIFSLLWVRIDPFTSRVTGPDILECGINC |

T942I: change from threonine to isoleucine at amino acid 942 (bolded and underlined)

| Portion of a CESA-3 from *Betula pendula* |
|---|
| MSQMNFEKKF GQSAIFVTST LMEQGGVPPS SSPAALLKEA IHVISCGYED SEQ ID NO: 4 |
| KTDWGLELGW IYGSITEDIL SGFKMHCRGW RSIYCMPKRP AFKGTAPINL |
| SDRLNQVLRW ALGSIEIFFS HHCPIWYGYK EGKLKWLERF SYVNTTVYPF |
| TSLPLLAYCT LPAICLLTDK FI.MPPISTF ASLYFIALFM SIFITGILEL |
| RWSGVTIEEW WRNEQFWVIG GVSAHLFAVF QGLLKVLAGI DTN▓▓▓T▓▓▓ |
| TDDE.DFGEL YTFKWTTLLI PPTTILIINL VGVVAGISDA INNGYESWGP |

| Portion of a CESA-3 from *Zea mays* |
|---|
| MSQMSLEKRF GQSAAFVAST LMEYGGVPQS ATPESLLKEA IHVISCGYED SEQ ID NO: 5 |
| KTEWGTEIGW IYGSVTEDIL TGFKMHARGW RSIYCMPKRP AFKGSAPINL |
| SDRLNQVLRW ALGSVEILFS RHCPLWYG. GGRLKFLERF AYINTTIYPL |
| TSIPLLIYCI LPAICLLTGK FI.IPEISNF ASIWFISLFI SIFATGILEM |
| RWSGVGIDEW WRNEQFWVIG GISAHLFAVF QGLLKVLAGI DTN▓▓▓T▓▓▓ |
| SDEDGDFAEL YMFKWTTLLI PPTTILIINL VGVVAGISYA INSGYQSWGP |

| Portion of a CESA-3 from *Arabidopsis thaliana* |
|---|
| MSQMSLEKRF GQSAVFVAST LMENGGVPPS ATPENLLKEA IHVISCGYED SEQ ID NO: 6 |
| KSDWGMEIGW IYGSVTEDIL TGFKMHARGW RSIYCMPKLP AFKGSAPINL |
| SDRLNQVLRW ALGSVEILFS RHCPIWYGY. NGRLKFLERF AYVNTTIYPI |
| TSIPLLMYCT LPAVCLFTNQ FI.IPQISNI ASIWFLSLFL SIFATGILEM |
| RWSGVGIDEW WRNEQFWVIG GVSAHLFAVF QGILKVLAGI DTN░░T░░ |
| SDEDGDFAEL YLFKWTTLLI PPTTLLIVNL VGVVAGVSYA INSGYQSWGP |

| Portion of a CESA-1 from *Arabidopsis thaliana* |
|---|
| MSQRSVEKRF GQSPVFIAAT FMEQGGIPPT TNPATLLKEA IHVISCGYED SEQ ID NO: 7 |
| KTEWGKEIGW IYGSVTEDIL TGFKMHARGW ISIYCNPPRP AFKGSAPINL |
| SDRLNQVLRW ALGSIEILLS RHCPIWYGY. HGRLRLLERI AYINTIVYPI |
| TSIPLIAYCI LPAFCLITDR FI.IPEISNY ASIWFILLFI SIAVTGILEL |
| RWSGVSIEDW WRNEQFWVIG GTSAHLFAVF QGLLKVLAGI DTN░░T░░ |
| TDEDGDFAEL YIFKWTALLI PPTTVLLVNL IGIVAGVSYA VNSGYQSWGP |

| Portion of a CESA-3 from *Populus trichocarpa* |
|---|
| MSQKSFEKRF GQSPVFIAST LMENGGVPEG TNSQSHIKEA IHVISCGYEE SEQ ID NO: 8 |
| KTEWGKEVGW IYGSVTEDIL TGFKMHCRGW RSVYCSPQRP AFKGSAPINL |
| SDRLHQVLRW ALGSIEIFLS HHCPLWYGY. GGKLKLLERL AYINTIVYPF |
| TSIPLLAYCT IPAVCLLTGK FI.IPTLNNL ASIWFLALFI SIIATSVLEL |
| RWSGVSIQDL WRNEQFWVIG GVSAHLFAVF QGLLKVLGGV DTN░░T░░ |
| AD.DAEFGEL YLFKWTTLLI PPTTLIILNM VGVVAGVSDA INNGYGSWGP |

| Portion of a CESA-3 from *Solanum lycopersicum* |
|---|
| MPQIKLEKKF GQSPVFVAST LLEDGGIPPG ATSASLLKEA IHVISCGYED SEQ ID NO: 9 |
| KTEWGKEIGW IYGSVTEDIL TGFKMHCHGW RSVYCMPDRP AFKGSAPINL |
| SDRLHQVLRW ALGSVEIFFS RHCPIWYGYG CG.LKPLERF SYINSVVYPL |
| TSIPLIIYCT LPAVFLLTRK FNWFPEISNY ASILFMGLFI MIAVTSVIEM |
| QWGGVSIDDW WRNEQFWVIG GASSHLFALF QGLLKVLAGV NTS░░T░░ |
| AD.DGEFSEL YLFKWTSLLI PPMTLLILNI IGVVVGVSDA INNGYDSWGP |

What is claimed is:

1. A method of processing plant cellulose, said method comprising extracting plant cellulose from a plant expressing a CESA polypeptide variant having an amino acid mutation selected from R1064W and A903V, wherein said amino acid mutation is in the carboxy-terminal transmembrane region of the CESA polypeptide variant; and
saccharifying the plant cellulose to produce fermentable sugars.

2. The method of claim 1, further comprising fermenting the fermentable sugars to produce alcohol.

3. The method of claim 1, wherein the plant cellulose has a measurable increase in saccharification efficiency relative to plant cellulose from a wild type plant.

4. The method of claim 3, wherein the plant cellulose has at least about a 1% increase in saccharification efficiency relative to plant cellulose from the wild type plant.

5. The method of claim 3, wherein the plant cellulose has at least about a 10% decrease in relative crystallinity relative to the wild type plant.

6. The method of claim 1, wherein the plant is a plant selected from the group consisting of: *Andropogon, Arabidopsis, Araucaria, Arundo, Aspidistra, Betula, Brachypodium, Chasmanthium, Cyanodon, Cynara, Eragrostis, Eucalyptus, Festuca, Miscanthus, Muhlenbergia, Nicotiana, Oryza, Panicum, Phalaris, Pinus, Pisum, Platanus, Podocarpus, Populus, Saccharum, Salix, Solanum, Sorghastrum, Sorghum, Spentina, Tripsacum*, and *Zea*.

7. A method of processing plant cellulose, said method comprising extracting plant cellulose from a plant expressing a CESA polypeptide variant having at least one amino acid mutation in its carboxy-terminal transmembrane region, selected from the group consisting of a CESA-1 polypeptide variant having a substitution at amino acid 903 from alanine to another amino acid; and a CESA-6 polypeptide variant having a substitution at amino acid 1064 from arginine to another amino acid; and
saccharifying the plant cellulose to produce fermentable sugars.

8. The method of claim 7, further comprising fermenting the fermentable sugars to produce alcohol.

9. The method of claim 7, wherein the plant cellulose has a measurable increase in saccharification efficiency relative to plant cellulose from a wild type plant.

10. The method of claim 7, wherein the plant cellulose has at least about a 1% increase in saccharification efficiency relative to plant cellulose from the wild type plant.

11. The method of claim 7, wherein the plant cellulose has at least about a 10% decrease in relative crystallinity relative to the wild type plant.

12. The method of claim 7, wherein the plant is a plant selected from the group consisting of: *Andropogon, Arabidopsis, Araucaria, Arundo, Aspidistra, Betula, Brachypodium, Chasmanthium, Cyanodon, Cynara, Eragrostis, Eucalyptus, Festuca, Miscanthus, Muhlenbergia, Nicotiana, Oryza, Panicum, Phalaris, Pinus, Pisum, Platanus, Podocarpus, Populus, Saccharum, Salix, Solanum, Sorghastrum, Sorghum, Spentina, Tripsacum*, and *Zea*.

13. The method of claim 7, wherein the at least one amino acid mutation includes a substitution at amino acid 903 from alanine to another amino acid.

14. The method of claim 13, wherein the at least one amino acid mutation includes a substitution at amino acid 903 from alanine to valine.

15. The method of claim 7, wherein the at least one amino acid mutation includes a substitution at amino acid 1064 from arginine to another amino acid.

16. The method of claim 15, wherein the at least one amino acid mutation includes a substitution at amino acid 1064 from arginine to tryptophan.

* * * * *